United States Patent
Namai

(10) Patent No.: US 9,529,259 B2
(45) Date of Patent: Dec. 27, 2016

(54) RADIATION-SENSITIVE RESIN COMPOSITION, RESIST PATTERN-FORMING METHOD, ACID DIFFUSION CONTROL AGENT, COMPOUND, AND METHOD FOR PRODUCING COMPOUND

(71) Applicant: JSR CORPORATION, Tokyo (JP)

(72) Inventor: Hayato Namai, Tokyo (JP)

(73) Assignee: JSR CORPORATION, Tokyo (JP)

( * ) Notice: Subject to any disclaimer, the term of this patent is extended or adjusted under 35 U.S.C. 154(b) by 0 days.

(21) Appl. No.: 14/827,795

(22) Filed: Aug. 17, 2015

(65) Prior Publication Data
US 2015/0355539 A1 Dec. 10, 2015

Related U.S. Application Data

(63) Continuation of application No. PCT/JP2014/056379, filed on Mar. 11, 2014.

(30) Foreign Application Priority Data

May 24, 2013 (JP) ................................ 2013-110437

(51) Int. Cl.
*G03F 7/004* (2006.01)
*G03F 7/039* (2006.01)
*G03F 7/20* (2006.01)
*G03F 7/30* (2006.01)
*G03F 7/32* (2006.01)
(Continued)

(52) U.S. Cl.
CPC ............. *G03F 7/0045* (2013.01); *C07C 51/02* (2013.01); *C07C 51/41* (2013.01); *C07C 59/185* (2013.01); *C07C 59/205* (2013.01); *C07C 59/21* (2013.01); *C07C 59/84* (2013.01); *C07C 67/30* (2013.01); *C07C 69/36* (2013.01); *C07C 69/63* (2013.01); *C07C 327/06* (2013.01); *C07C 327/32* (2013.01); *C07C 381/12* (2013.01); *C07D 307/77* (2013.01); *C07D 307/93* (2013.01); *C07D 313/04* (2013.01); *C07D 313/10* (2013.01); *C07D 315/00* (2013.01); *C07D 317/46* (2013.01); *C07D 317/72* (2013.01); *C07D 327/04* (2013.01); *C08F 2/38* (2013.01); *C08F 4/00* (2013.01); *C08F 12/24* (2013.01); *C08F 212/14* (2013.01); *G03F 7/004* (2013.01); *G03F 7/038* (2013.01); *G03F 7/039* (2013.01); *G03F 7/0397* (2013.01); *G03F 7/2041* (2013.01); *G03F 7/30* (2013.01); *G03F 7/322* (2013.01); *G03F 7/325* (2013.01); *C07C 2101/08* (2013.01); *C07C 2101/14* (2013.01); *C07C 2101/18* (2013.01); *C07C 2103/74* (2013.01)

(58) Field of Classification Search
None
See application file for complete search history.

(56) References Cited

U.S. PATENT DOCUMENTS 6,280,900 B1 * 8/2001 Chiba .................... G03F 7/0045
430/270.1
2005/0016402 A1 * 1/2005 Oshima ................. B41C 1/1008
101/453

FOREIGN PATENT DOCUMENTS

JP H08-146610 A 6/1996
JP H11-125907 A 5/1999
(Continued)

OTHER PUBLICATIONS

International Search Report issued Jun. 10, 2014, in PCT/JP2014/056379 (w/ English translation).

*Primary Examiner* — Sin Lee
(74) *Attorney, Agent, or Firm* — Oblon, McClelland, Maier & Neustadt, L.L.P.

(57) ABSTRACT

A radiation-sensitive resin composition includes a polymer including a structural unit that includes an acid-labile group; and a compound represented by formula (1). $R^1$ represents a monovalent organic group having 1 to 30 carbon atoms. L represents a single bond, an oxygen atom or a sulfur atom. $M^+$ represents a monovalent radioactive ray-labile onium cation. The monovalent organic group represented by $R^1$ is preferably a monovalent hydrocarbon group or a monovalent fluorinated hydrocarbon group, and L preferably represents a single bond. The monovalent organic group represented by $R^1$ is preferably a monovalent hydrocarbon group, a monovalent fluorinated hydrocarbon group, a monovalent aliphatic heterocyclic group or a monovalent fluorinated aliphatic heterocyclic group, and L preferably represents an oxygen atom or a sulfur atom. The monovalent radioactive ray-labile onium cation represented by $M^+$ is preferably represented by the formula (X).

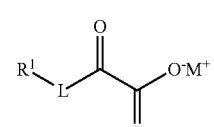

(1)

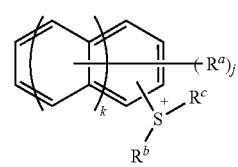

(X)

15 Claims, No Drawings

(51) Int. Cl.

| | | |
|---|---|---|
| C07C 59/185 | (2006.01) | |
| C07C 59/205 | (2006.01) | |
| C07C 59/84 | (2006.01) | |
| C07C 59/21 | (2006.01) | |
| C07C 69/36 | (2006.01) | |
| C07C 381/12 | (2006.01) | |
| C07D 307/77 | (2006.01) | |
| C07D 313/04 | (2006.01) | |
| C07D 317/46 | (2006.01) | |
| C07D 317/72 | (2006.01) | |
| C07D 327/04 | (2006.01) | |
| C07D 313/10 | (2006.01) | |
| C07D 307/93 | (2006.01) | |
| C07D 315/00 | (2006.01) | |
| C07C 51/41 | (2006.01) | |
| C07C 327/32 | (2006.01) | |
| C07C 67/30 | (2006.01) | |
| C07C 51/02 | (2006.01) | |
| C08F 212/14 | (2006.01) | |
| G03F 7/038 | (2006.01) | |
| C08F 2/38 | (2006.01) | |
| C08F 4/00 | (2006.01) | |
| C07C 69/63 | (2006.01) | |
| C07C 327/06 | (2006.01) | |
| C08F 12/24 | (2006.01) | |

(56) References Cited

FOREIGN PATENT DOCUMENTS

| | | |
|---|---|---|
| JP | 2000-298347 A | 10/2000 |
| JP | 2001-013687 A | 1/2001 |
| JP | 2002-148790 A | 5/2002 |
| JP | 2005-014603 A | 1/2005 |

* cited by examiner

RADIATION-SENSITIVE RESIN COMPOSITION, RESIST PATTERN-FORMING METHOD, ACID DIFFUSION CONTROL AGENT, COMPOUND, AND METHOD FOR PRODUCING COMPOUND

CROSS-REFERENCE TO RELATED APPLICATIONS

The present application is a continuation application of International Application No. PCT/JP2014/056379, filed Mar. 11, 2014, which claims priority to Japanese Patent Application No. 2013-110437, filed May 24, 2013. The contents of these applications are incorporated herein by reference in their entirety.

BACKGROUND OF THE INVENTION

Field of the Invention

The present invention relates to a radiation-sensitive resin composition, a resist pattern-forming method, an acid diffusion control agent, a compound, and a method for producing the compound.

Discussion of the Background

In radiation-sensitive resin compositions for use in microfabrication by lithography, an acid is generated at a light-exposed site upon irradiation with a far ultraviolet ray such as an ArF excimer laser beam or a KrF excimer laser beam, an extreme ultraviolet ray (EUV) or a charged particle ray such as an electron beam, and the like, and chemical reactions catalyzed by the acid produce a difference in a rate of dissolution in a developer solution between the light-exposed site and a light-unexposed site, thereby enabling a resist pattern to be formed on a substrate.

For such radiation-sensitive resin compositions, an improvement of a resolution, and rectangularity of a cross-sectional shape of a resist pattern has been demanded with the advance of microfabrication technologies. To address the demand, the type and/or the molecular structure of a polymer, an acid generating agent and other component for use in the composition have been investigated, and further a combination thereof has also been investigated in detail (see Japanese Unexamined Patent Application, Publication Nos. H11-125907, H08-146610, and 2000-298347).

In such a current situation in which microfabrication of resist patterns has been further in progress, the resolution and the rectangularity of a cross-sectional shape have not been sufficiently satisfied. In addition, superior line width roughness (LWR) performance, in which LWR is an indicative of variations of line widths in a resist pattern is also demanded, and furthermore, an improvement of a depth of focus is also demanded for the purpose of improving process stability.

SUMMARY OF THE INVENTION

According to one aspect of the present invention, a radiation-sensitive resin composition includes a polymer that includes a structural unit that includes an acid-labile group, and a compound represented by formula (1).

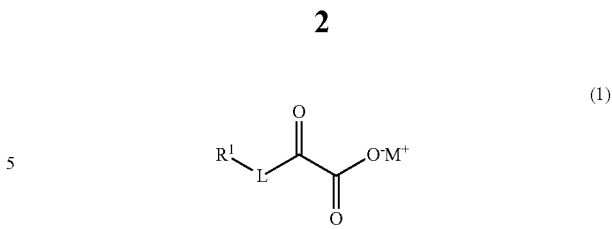

In the formula (1), $R^1$ represents a monovalent organic group having 1 to 30 carbon atoms; L represents a single bond, an oxygen atom or a sulfur atom; and $M^+$ represents a monovalent radioactive ray-labile onium cation.

According to another aspect of the present invention, a resist pattern-forming method includes providing a resist film using the radiation-sensitive resin composition. The resist film is exposed. The exposed resist film is developed.

According to further aspect of the present invention, an acid diffusion control agent includes a compound represented by formula (1).

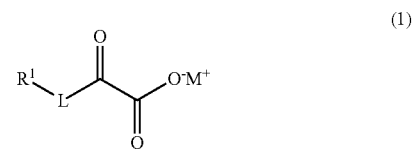

In the formula (1), $R^1$ represents a monovalent organic group having 1 to 30 carbon atoms; L represents a single bond, an oxygen atom or a sulfur atom; and $M^+$ represents a monovalent radioactive ray-labile onium cation.

According to further aspect of the present invention, a compound is represented by formula (1).

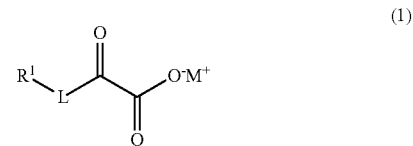

In the formula (1), $R^1$ represents a monovalent organic group having 1 to 30 carbon atoms; L represents a single bond, an oxygen atom or a sulfur atom; and $M^+$ represents a monovalent radioactive ray-labile onium cation.

According to further aspect of the present invention, a method for producing a compound represented by formula (1), includes reacting a compound represented by formula (1a) with a compound represented by formula (1b) to produce the compound represented by formula (1).

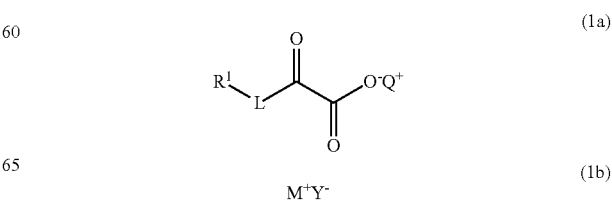

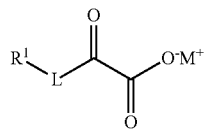

(1)

In the formulae (1a), (1b) and (1), $R^1$ represents a monovalent organic group having 1 to 30 carbon atoms; L represents a single bond, an oxygen atom or a sulfur atom; $Q^+$ represents a monovalent alkali metal cation or a monovalent organic ammonium cation; $M^+$ represents a monovalent radioactive ray-labile onium cation; and $Y^-$ represents a monovalent halogen anion or a monovalent methylsulfuric acid anion.

DESCRIPTION OF THE EMBODIMENTS

According to an embodiment of the invention, a radiation-sensitive resin composition contains:

a polymer (hereinafter, may be also referred to as "(A) polymer" or "polymer (A)") having a structural unit that includes an acid-labile group (hereinafter, may be also referred to as "structural unit (I)"): and a compound represented by the following formula (1) (hereinafter, may be also referred to as "(B) compound" or "compound (B)"),

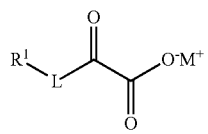

(1)

wherein in the formula (1), $R^1$ represents a monovalent organic group having 1 to 30 carbon atoms; L represents a single bond, an oxygen atom or a sulfur atom; and $M^+$ represents a monovalent radioactive ray-labile onium cation.

According to another embodiment of the present invention, a resist pattern-forming method includes:

providing a resist film;
exposing the resist film; and
developing the exposed resist film, wherein the resist film is provided using the radiation-sensitive resin composition according to the embodiment of the present invention.

According to still another embodiment of the present invention, an acid diffusion control agent contains a compound represented by the following formula (1):

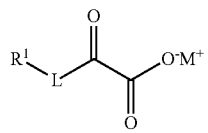

(1)

wherein in the formula (1), $R^1$ represents a monovalent organic group having 1 to 30 carbon atoms; L represents a single bond, an oxygen atom or a sulfur atom; and $M^+$ represents a monovalent radioactive ray-labile onium cation.

According to yet still another embodiment of the present invention, a compound is represented by the following formula (1):

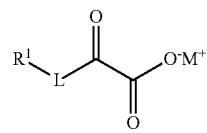

(1)

wherein in the formula (1), $R^1$ represents a monovalent organic group having 1 to 30 carbon atoms; L represents a single bond, an oxygen atom or a sulfur atom; and $M^+$ represents a monovalent radioactive ray-labile onium cation.

According to even yet still another embodiment of the present invention, a method for producing a compound represented by the following formula (1) includes:

reacting a compound represented by the following formula (1a) with a compound represented by the following formula (1b),

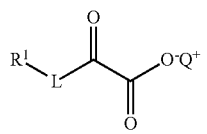

(1a)

(1b)

$M^+Y^-$

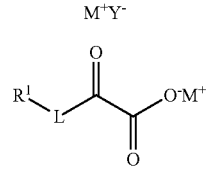

(1)

wherein in the formulae (1a), (1b) and (1), $R^1$ represents a monovalent organic group having 1 to 30 carbon atoms; L represents a single bond, an oxygen atom or a sulfur atom; $Q^+$ represents a monovalent alkali metal cation or a monovalent organic ammonium cation; $M^+$ represents a monovalent radioactive ray-labile onium cation; and $Y^-$ represents a monovalent halogen anion or a monovalent methylsulfuric acid anion.

The "organic group" as referred to herein means a group that includes at least one carbon atom.

The radiation-sensitive resin composition and the resist pattern-forming method according to the embodiments of the present invention enable a resist pattern having a small LWR, high resolution, and superior rectangularity of a cross-sectional shape to be formed while exhibiting a great depth of focus. The acid diffusion control agent according to the embodiment of the present invention can be suitably used as a component of the radiation-sensitive resin composition according to the embodiment of the present invention. The compound according to the embodiment of the present invention can be suitably used as the acid diffusion control agent according to the embodiment of the present invention. The method for producing a compound according to the embodiment of the present invention enables the compound to be produced conveniently in a favorable yield. Therefore, these can be suitably used in processes for production of semiconductor devices, and the like, in which further progress of miniaturization is expected in the future. Hereinafter, embodiments of the present invention will be described in detail.

Radiation-Sensitive Resin Composition

A radiation-sensitive resin composition according to an embodiment of the present invention contains (A) a polymer and (B) a compound. In addition, the radiation-sensitive resin composition may contain, as favorable components, (C) a radiation-sensitive acid generator, (D) an acid diffusion control agent constituted with a compound other than the compound (B) (hereinafter, may be also referred to as "(D) other acid diffusion control agent" or "other acid diffusion control agent (D)"), (E) a fluorine atom-containing polymer (hereinafter, may be also referred to as "(E) polymer" or "polymer (E)"), and (F) a solvent, and may contain other optional component within a range not leading to impairment of the effects of the present invention. Hereinafter, each component will be explained.

(A) Polymer

The polymer (A) has the structural unit (I). According to the radiation-sensitive resin composition, an acid-labile group of the polymer (A) at a light-exposed site is dissociated upon irradiation with a radioactive ray, causing a difference in solubility in a developer solution to be produced between the light-exposed site and a light-unexposed site, and consequently a resist pattern can be formed. The "acid-labile group" as referred to means a group that substitutes for a hydrogen atom of a carboxy group, hydroxy group or the like and is dissociated by the action of an acid. The polymer (A) is not particularly limited as long as it includes an acid-labile group, and the acid-labile group may be present at any position i.e., in the main chain, in a side chain, at an end, etc., of the polymer (A). The polymer (A) may have, in addition to the structural unit (I): a structural unit (II) that includes a nonlabile and polar group; a structural unit (III) represented by the following formula (4) described later; and a structural unit other than the structural units (I) to (III). The polymer (A) may have either one, or two or more types of each structural unit. Hereinafter, each structural unit will be explained.

Structural Unit (I)

The structural unit (I) includes an acid-labile group. The structural unit (I) is exemplified by a structural unit represented by the following formula (2-1) (hereinafter, may be also referred to as "structural unit (I-1)"), a structural unit represented by the following formula (2-2) (hereinafter, may be also referred to as "structural unit (I-2)"), and the like.

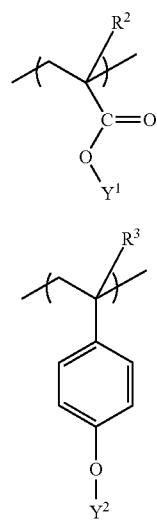

In the above formula (2-1), $R^2$ represents a hydrogen atom, a fluorine atom, a methyl group or a trifluoromethyl group; and $Y^1$ represents a monovalent acid-labile group.

In the above formula (2-2), $R^3$ represents a hydrogen atom or a methyl group; and $Y^2$ represents a monovalent acid-labile group.

In light of the copolymerizability of a monomer that gives the structural unit (I-1), $R^2$ represents preferably a hydrogen atom or a methyl group, and more preferably a methyl group.

The monovalent acid-labile group represented by $Y^1$ is preferably a group represented by the following formula (Y-1).

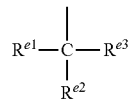

(Y-1)

In the above formula (Y-1), $R^{e1}$ represents a monovalent hydrocarbon group having 1 to 20 carbon atoms; and $R^{e2}$ and $R^{e3}$ each independently represent a monovalent chain hydrocarbon group having 1 to 10 carbon atoms or a monovalent alicyclic hydrocarbon group having 3 to 20 carbon atoms, or $R^{e2}$ and $R^{e3}$ taken together represent an alicyclic structure having 3 to 20 ring carbon atoms together with the carbon atom to which $R^{e2}$ and $R^{e3}$ bond.

The monovalent hydrocarbon group having 1 to 20 carbon atoms which is represented by $R^{e1}$ is exemplified by a monovalent chain hydrocarbon group having 1 to 10 carbon atoms, a monovalent alicyclic hydrocarbon group having 3 to 20 carbon atoms, a monovalent aromatic hydrocarbon group having 6 to 20 carbon atoms, and the like.

Examples of the monovalent chain hydrocarbon group having 1 to 10 carbon atoms which may be represented by $R^{e1}$, $R^{e2}$ or $R^{e3}$ include:

alkyl groups such as a methyl group, an ethyl group, a n-propyl group, an i-propyl group, a n-butyl group, an i-butyl group, a sec-butyl group, a t-butyl group and a n-pentyl group;

alkenyl groups such as an ethenyl group, a propenyl group, a butenyl group and a pentenyl group;

alkynyl groups such as an ethynyl group, a propynyl group, a butynyl group and a pentynyl group; and the like.

Of these, alkyl groups are preferred, alkyl groups having 1 to 4 carbon atoms are more preferred, a methyl group, an ethyl group and an i-propyl group are still more preferred, and an ethyl group is particularly preferred.

Examples of the monovalent alicyclic hydrocarbon group having 3 to 20 carbon atoms which may be represented by $R^{e1}$, $R^{e2}$ or $R^{e3}$ include:

monocyclic cycloalkyl groups such as a cyclopropyl group, a cyclobutyl group, a cyclopentyl group, a cyclohexyl group and a cyclooctyl group;

polycyclic cycloalkyl groups such as a norbornyl group, an adamantyl group, a tricyclodecyl group and a tetracyclododecyl group;

monocyclic cycloalkenyl groups such as a cyclopropenyl group, a cyclobutenyl group, a cyclopentenyl group and a cyclohexenyl group;

polycyclic cycloalkenyl groups such as a norbornenyl group and a tricyclodecenyl group; and the like.

Of these, monocyclic cycloalkyl groups and polycyclic cycloalkyl groups are preferred, and a cyclopentyl group, a cyclohexyl group, a norbornyl group and an adamantyl group are more preferred.

Examples of the monovalent aromatic hydrocarbon group having 6 to 20 carbon atoms which may be represented by $R^{e1}$ include:

aryl groups such as a phenyl group, a tolyl group, a xylyl group, a naphthyl group and an anthryl group;

aralkyl groups such as a benzyl group, a phenethyl group and a naphthylmethyl group; and the like.

Examples of the alicyclic structure having 3 to 20 ring carbon atoms which may be taken together represented by $R^{e2}$ and $R^{e3}$ together with the carbon atom to which $R^{e2}$ and $R^{e3}$ bond include:

monocyclic cycloalkane structures such as a cyclopropane structure, a cyclobutane structure, a cyclopentane structure, a cyclohexane structure and a cyclooctane structure;

polycyclic cycloalkane structures such as a norbornane structure, an adamantane structure, a tricyclodecane structure and a tetracyclododecane structure;

monocyclic cycloalkene structures such as a cyclopropene structure, a cyclobutene structure, a cyclopentene structure, a cyclohexene structure and a cyclooctene structure;

polycyclic cycloalkene structures such as a norbornene structure, a tricyclodecene structure and a tetracyclododecene structure; and the like.

Of these, monocyclic cycloalkane structures and polycyclic cycloalkane structures are preferred, monocyclic cycloalkane structures having 5 to 8 carbon atoms and polycyclic cycloalkane structures having 7 to 12 carbon atoms are more preferred, and a cyclopentane structure, a cyclohexane structure, a cyclooctane structure, a norbornane structure and an adamantane structure are still more preferred, and a cyclopentane structure and an adamantane structure are particularly preferred.

It is to be noted that the alicyclic structure may have a substituent. Examples of the substituent include a hydroxy group, a carboxy group, a cyano group, and the like.

The group represented by the above formula (Y-1) is preferably a group represented by the above formula (Y-1) in which $R^{e1}$ represents a monovalent chain hydrocarbon group having 1 to 10 carbon atoms, and $R^{e2}$ and $R^{e3}$ taken together represent an alicyclic structure having 3 to 20 ring carbon atoms together with the carbon atom to which $R^{e2}$ and $R^{e3}$ bond, more preferably a group represented by the above formula (Y-1) in which $R^{e1}$ represents an alkyl group having 1 to 10 carbon atoms, and $R^{e2}$ and $R^{e3}$ taken together represent a cycloalkane structure having 3 to 20 ring carbon atoms together with the carbon atom to which $R^{e2}$ and $R^{e3}$ bond, still more preferably a group represented by the above formula (Y-1) in which $R^{e1}$ represents an alkyl group having 1 to 4 carbon atoms, and $R^{e2}$ and $R^{e3}$ taken together represent a monocyclic cycloalkane structure having 5 to 8 ring carbon atoms or a polycyclic cycloalkane structure having 7 to 12 ring carbon atoms together with the carbon atom to which $R^{e2}$ and $R^{e3}$ bond, and particularly preferably a 1-ethyl-1-cyclopentyl group or a 2-ethyl-2-adamantyl group.

In light of the copolymerizability of a monomer that gives the structural unit (I-2), $R^3$ preferably represents a hydrogen atom.

The monovalent acid-labile group represented by $Y^2$ is preferably a group represented by the following formula (Y-2).

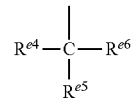

(Y-2)

In the above formula (Y-2), $R^{e4}$, $R^{e5}$ and $R^{e6}$ each independently represent a hydrogen atom, a monovalent chain hydrocarbon group having 1 to 20 carbon atoms, a monovalent alicyclic hydrocarbon group having 3 to 20 carbon atoms, a chain oxyhydrocarbon group or an alicyclic oxyhydrocarbon group having 1 to 20 carbon atoms having 1 to 20 carbon atoms, wherein at least one of $R^{e4}$, $R^{e5}$ and $R^{e6}$ does not represent a hydrogen atom.

Examples of the monovalent chain hydrocarbon group having 1 to 20 carbon atoms which may be represented by $R^{e4}$, $R^{e5}$ or $R^{e6}$ include:

alkyl groups such as a methyl group, an ethyl group, a n-propyl group, an i-propyl group, a n-butyl group, an i-butyl group, a sec-butyl group, a t-butyl group and a n-pentyl group;

alkenyl groups such as an ethenyl group, a propenyl group, a butenyl group and a pentenyl group;

alkynyl groups such as an ethynyl group, a propynyl group, a butynyl group and a pentynyl group; and the like.

Of these, alkyl groups are preferred, alkyl groups having 1 to 4 carbon atoms are more preferred, a methyl group, an ethyl group and a n-propyl group are still more preferred, and a methyl group is particularly preferred.

Examples of the monovalent alicyclic hydrocarbon group having 3 to 20 carbon atoms which may be represented by $R^{e4}$, $R^{e5}$ or $R^{e6}$ include monovalent alicyclic hydrocarbon groups similar to those exemplified in connection with $R^{e1}$, $R^{e2}$ and $R^{e3}$, and the like.

Of these, monocyclic cycloalkyl groups and polycyclic cycloalkyl groups are preferred, and a cyclopentyl group, a cyclohexyl group, a norbornyl group and an adamantyl group are more preferred.

Examples of the monovalent chain oxyhydrocarbon group having 1 to 20 carbon atoms which may be represented by $R^{e4}$, $R^{e5}$ or $R^{e6}$ include:

alkoxy groups such as a methoxy group, an ethoxy group, a n-propoxy group, an i-propoxy group, a n-butoxy group, an i-butoxy group, a sec-butoxy group, a t-butoxy group and a n-pentyloxy group;

alkenyloxy groups such as an ethenyloxy group, a propenyloxy group, a butenyloxy group and a pentenyloxy group;

alkynyloxy groups such as an ethynyloxy group, a propynyloxy group, a butynyloxy group and a pentynyloxy group; and the like.

Of these, alkoxy groups are preferred, alkoxy group having 1 to 4 carbon atoms are more preferred, and a methoxy group, an ethoxy group and a n-propoxy group are still more preferred.

Examples of the monovalent alicyclic oxyhydrocarbon group having 3 to 20 carbon atoms which may be represented by $R^{e4}$, $R^{e5}$ or $R^{e6}$ include:

monocyclic cycloalkyloxy groups such as a cyclopropyloxy group, a cyclobutyloxy group, a cyclopentyloxy group, a cyclohexyloxy group and a cyclooctyloxy group;

polycyclic cycloalkyloxy groups such as a norbornyloxy group, an adamantyloxy group, a tricyclodecyloxy group and a tetracyclododecyloxy group;

monocyclic cycloalkenyloxy groups such as a cyclopropenyloxy group, a cyclobutenyloxy group, a cyclopentenyloxy group and a cyclohexenyloxy group;

polycyclic cycloalkenyloxy groups such as a norbornenyloxy group and a tricyclodecenyloxy group; and the like.

Of these, monocyclic cycloalkyloxy groups and polycyclic cycloalkyloxy groups are preferred, and a cyclopentyloxy group, a cyclohexyloxy group, a norbornyloxy group and an adamantyloxy group are more preferred.

The group represented by the above formula (Y-2) is preferably a group represented by the above formula (Y-2) in which $R^{e4}$, $R^{e5}$ and $R^{e6}$ represent a monovalent chain hydrocarbon group, a group represented by the above formula (Y-2) in which $R^{e4}$ and $R^{e5}$ represent a monovalent chain hydrocarbon group and $R^{e6}$ represents a monovalent chain oxyhydrocarbon group, or a group represented by the above formula (Y-2) in which $R^{e4}$ represents a monovalent chain hydrocarbon group, and $R^{e5}$ and $R^{e6}$ represent a monovalent chain oxyhydrocarbon group, more preferably a group represented by the above formula (Y-2) in which $R^{e4}$, $R^{e5}$ and $R^{e6}$ represent an alkyl group, a group represented by the above formula (Y-2) in which $R^{e4}$ and $R^{e5}$ represent an alkyl group and $R^{e6}$ represents an alkoxy group, or a group represented by the above formula (Y-2) in which $R^{e4}$ represents an alkyl group, and $R^{e5}$ and $R^{e6}$ represent an alkoxy group, still more preferably a group represented by the above formula (Y-2) in which $R^{e4}$, $R^{e5}$ and $R^{e6}$ represent an alkyl group, and particularly preferably a t-butyl group, a t-pentyl group, a t-hexyl group or a t-heptyl group.

Examples of the structural unit (I) include:

structural units represented by the following formulae (2-1-1) to (2-1-7), and the like as the structural unit (I-1);

the structural units represented by the following formulae (2-2-1) to (2-2-3), and the like as the structural unit (I-2).

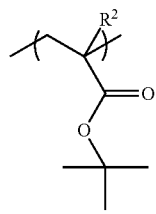

(2-1-1)

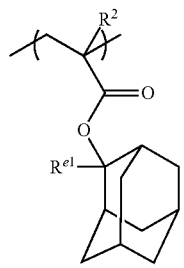

(2-1-2)

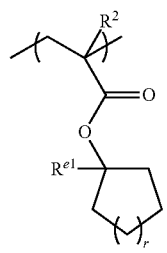

(2-1-3)

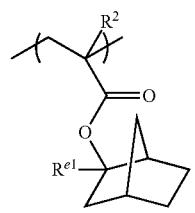

(2-1-4)

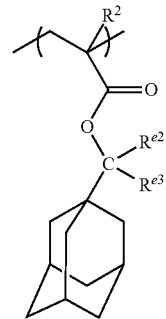

(2-1-5)

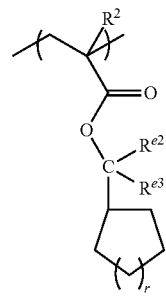

(2-1-6)

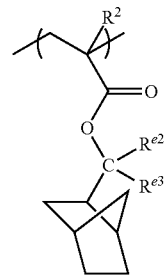

(2-1-7)

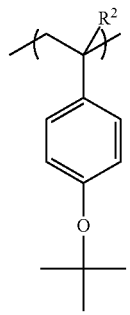

(2-2-1)

(2-2-2)

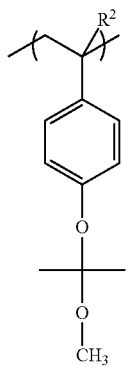

(2-2-3)

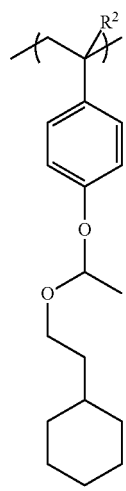

In the above formulae (2-1-1) to (2-1-7), $R^2$ is as defined in the above formula (2-1); $R^{e1}$, $R^{e2}$ and $R^{e3}$ are as defined in the above formula (Y-1); and "r"s are each independently an integer of 1 to 3.

In the above formulae (2-2-1) to (2-2-3), $R^3$ is as defined in the above formula (2-2).

The structural unit (I) is preferably the structural unit (I-1), more preferably the structural unit represented by the above formula (2-1-2) or the structural unit represented by the above formula (2-1-3), still more preferably a group that includes a cyclopentane structure, or a group that includes an adamantane structure, and particularly preferably a structural unit derived from 1-ethyl-1-cyclopentyl (meth)acrylate, or a structural unit derived from 2-ethyl-2-adamantyl (meth)acrylate.

The proportion of the structural unit (I) is preferably 10 mol % to 90 mol %, more preferably 20 mol % to 70 mol %, still more preferably 30 mol % to 60 mol %, and particularly preferably 40 mol % to 60 mol % with respect to the total structural units constituting the polymer (A). When the proportion of the structural unit (I) falls within the above range, the LWR performance, the resolution, the rectangularity of a cross-sectional shape, and the depth of focus of the radiation-sensitive resin composition can be improved.

Structural Unit (II)

The structural unit (II) includes a nonlabile and polar group. When the polymer (A) has the structural unit (II), dispersibility of the compound (B) in the polymer (A) can be improved. As a result, the radiation-sensitive resin composition can exhibit improved LWR performance, resolution, rectangularity of a cross-sectional shape, and depth of focus. In addition, a resist pattern formed from the radiation-sensitive resin composition may exhibit improved adhesiveness to a substrate. The structural unit (II) is exemplified by a structural unit represented by the following formula (3-1) (hereinafter, may be also referred to as "structural unit (II-1)"), a structural unit represented by the following formula (3-2) (hereinafter, may be also referred to as "structural unit (II-2)"), and the like.

(3-1)

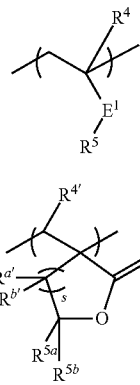

(3-2)

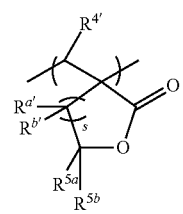

In the above formula (3-1), $R^4$ represents a hydrogen atom, a fluorine atom, a methyl group or a trifluoromethyl group; $E^1$ represents a single bond, —CO—O—, —CO—NH— or —CO—O—$(CH_2)_i$—CO—O—, wherein "i" is an integer of 1 to 6; and $R^5$ represents an acid-nonlabile group that includes a polar group.

In the above formula (3-2), $R^{4'}$ represents a hydrogen atom or a methyl group; $R^{a'}$ and $R^{b'}$ each independently represent a hydrogen atom, a fluorine atom, a hydroxy group or a monovalent organic group; "s" is an integer of 1 to 3, wherein in a case where "s" is no less than 2, a plurality of $R^{a'}$s may be each identical or different, and a plurality of $R^{b'}$s may be each identical or different; and $R^{5a}$ and $R^{5b}$ each independently represent a hydrogen atom, a fluorine atom, a hydroxy group or a monovalent organic group.

In the structural unit (II-1), in light of the copolymerizability of a monomer that gives the structural unit (II-1), $R^4$ represents preferably a hydrogen atom or a methyl group, and still more preferably a methyl group.

In light of the copolymerizability of a monomer that gives the structural unit (II-1), $E^1$ preferably represents —CO—O—.

Examples of the polar group in the acid-nonlabile group that includes a polar group, which is represented by $R^5$, include: (a) monovalent groups such as a hydroxy group, a carboxy group, a cyano group, a sulfo group, a mercapto group and an amino group; (b) divalent groups such as a carbonyl group, —O—, —S—, —NR'—, and a combination thereof, wherein R' represents a hydrogen atom or a monovalent hydrocarbon group having 1 to 20 carbon atoms; and the like.

Examples of the acid-nonlabile group that includes a polar group, which is represented by $R^5$, include: groups obtained from a monovalent hydrocarbon group having 1 to 20 carbon atoms by substituting a part or all of hydrogen atoms included therein with the monovalent group (a); groups obtained from a monovalent hydrocarbon group having 1 to 20 carbon atoms by incorporating the divalent group (b) between any or every adjacent two carbons thereof; groups obtained from a monovalent hydrocarbon group having 1 to 20 carbon atoms by substituting a part or all of hydrogen atoms included therein with the monovalent group (a), and incorporating the divalent group (b) between any or every adjacent two carbons thereof; and the like.

The monovalent hydrocarbon group having 1 to 20 carbon atoms is exemplified by a monovalent chain hydrocarbon group having 1 to 20 carbon atoms, a monovalent alicyclic hydrocarbon group having 3 to 20 carbon atoms, a monovalent aromatic hydrocarbon group having 6 to 20 carbon atoms, and the like.

Examples of the monovalent chain hydrocarbon group having 1 to 20 carbon atoms include monovalent chain hydrocarbon groups similar to those exemplified in connection with $R^{e4}$, $R^{e5}$ and $R^{e6}$ in the above formula (2-2), and the like.

Examples of the monovalent alicyclic hydrocarbon group having 3 to 20 carbon atoms include monovalent alicyclic hydrocarbon groups similar to those exemplified in connection with $R^{e1}$, $R^{e2}$ and $R^{e3}$ in the above formula (2-1), and the like.

Examples of the monovalent aromatic hydrocarbon group having 6 to 20 carbon atoms include:

aryl groups such as a phenyl group, a tolyl group, a xylyl group, a mesityl group, a naphthyl group, a methylnaphthyl group, an anthryl group and a methylanthryl group;

aralkyl groups such as a benzyl group, a phenethyl group, a naphthylmethyl group and an anthrylmethyl group; and the like.

$R^5$ is exemplified by a group that includes a lactone structure, a group that includes a cyclic carbonate structure, a group that includes a sultone structure, a group that includes a hydroxy group, and the like.

Examples of the group that includes a lactone structure include a butyrolactone-yl group, a norbornanelactone-yl group, a 5-oxo-4-oxatricyclo[4.3.1.1$^{3,8}$]undecan-yl group, and the like.

Examples of the group that includes a cyclic carbonate structure include ethylene carbonate-ylmethyl group, and the like.

Examples of the group that includes a sultone structure include groups that include a sultone structure, such as a propane sultone-yl group, a norbornanesultone-yl group, and the like.

Examples of the group that includes a hydroxy group include a hydroxyadamantyl group, a dihydroxyadamantyl group, a trihydroxyadamantyl group, a hydroxyethyl group, and the like.

In the structural unit (II-2), in light of the copolymerizability of a monomer that gives the structural unit (II-2), $R^{4'}$ preferably represents a hydrogen atom.

The monovalent organic group which may be represented by $R^{a'}$, $R^{b'}$, $R^{5a}$ or $R^{5b}$ is exemplified by: a monovalent chain hydrocarbon group having 1 to 20 carbon atoms; a monovalent alicyclic hydrocarbon group having 3 to 20 carbon atoms; a monovalent aromatic hydrocarbon group having 6 to 20 carbon atoms; a group obtained from the monovalent chain hydrocarbon group, the monovalent alicyclic hydrocarbon group or the monovalent aromatic hydrocarbon group by substituting a part or all of hydrogen atoms included therein with a substituent; a group obtained from the monovalent chain hydrocarbon group, the monovalent alicyclic hydrocarbon group or the monovalent aromatic hydrocarbon group by incorporating —CO—, —CS—, —O—, —S— or —NR"—, or a combination of two or more thereof between adjacent two carbons thereof; and the like, wherein R" represents a hydrogen atom or a monovalent hydrocarbon group having 1 to 20 carbon atoms.

Preferably, "s" is 1 or 2, and more preferably 1.

Examples of the structural unit (II) include:

structural units represented by the following formulae (3-1-1) to (3-1-13), and the like as the structural unit (II-1); and structural units represented by the following formulae (3-2-1) and (3-2-2), and the like as the structural unit (II-2).

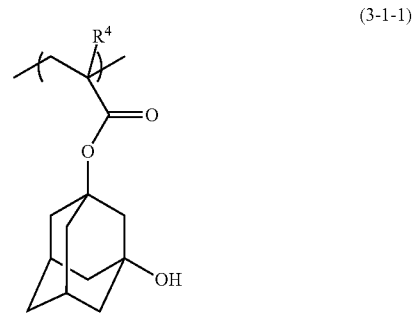

(3-1-1)

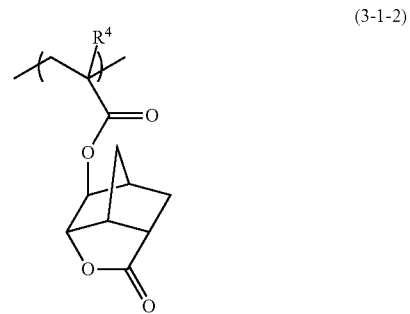

(3-1-2)

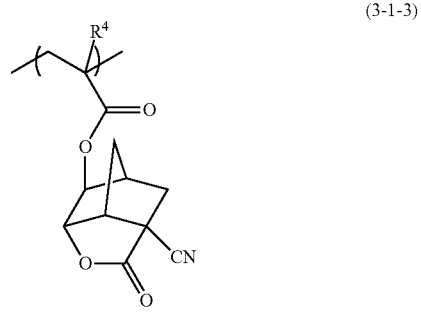

(3-1-3)

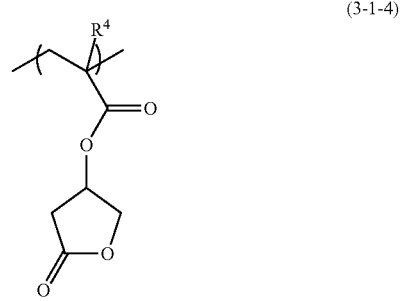

(3-1-4)

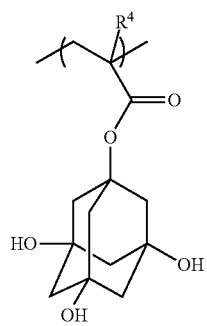 (3-1-5)
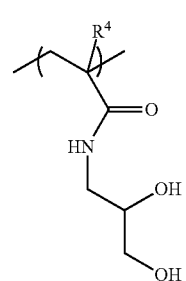 (3-1-6)
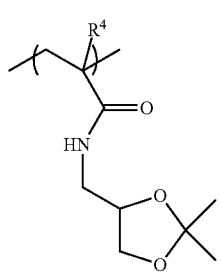 (3-1-7)
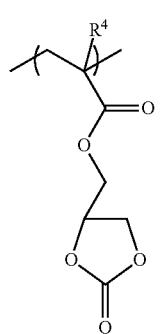 (3-1-8)
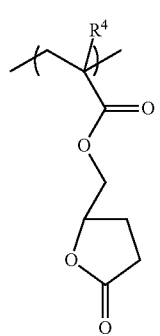 (3-1-9)
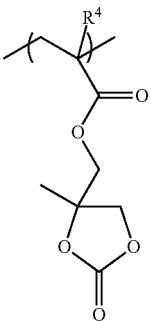 (3-1-10)
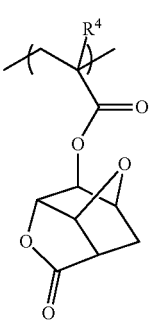 (3-1-11)
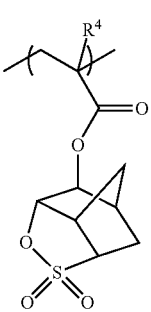 (3-1-12)
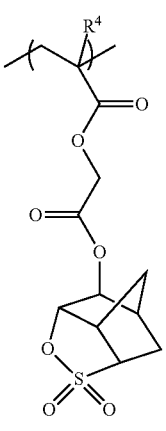 (3-1-13)
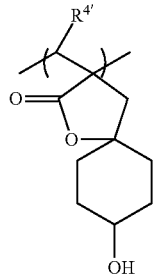 (3-2-1)

-continued

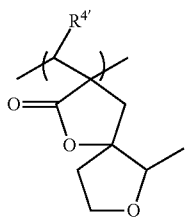
(3-2-2)

In the above formulae (3-1-1) to (3-1-13), $R^4$ is as defined in the above formula (3-1).

In the above formulae (3-2-1) and (3-2-2), $R^{4'}$ is as defined in the above formula (3-2).

Of these, the structural units represented by the above formulae (3-1-1) to (3-1-4), (3-1-8), (3-1-12), (3-1-13), (3-2-1), and (3-2-2) are preferred, and the structural unit represented by the above formula (3-2) is more preferred.

The proportion of the structural unit (II) is preferably 0 mol % to 90 mol %, more preferably 20 mol % to 70 mol %, and still more preferably 30 mol % to 60 mol % with respect to the total structural units constituting the polymer (A). When the proportion of the structural unit (II) falls within the above range, dispersibility of the compound (B) and the like in the polymer (A) may be further improved, and as a result, the performances such as the LWR performance of the radiation-sensitive resin composition can be further improved.

Structural Unit (III)

The structural unit (III) is represented by the following formula (4). In a case where a KrF excimer laser beam, EUV, an electron beam or the like is employed as a radioactive ray for irradiation, when the polymer (A) has the structural unit (III), the sensitivity of the radiation-sensitive resin composition can be increased.

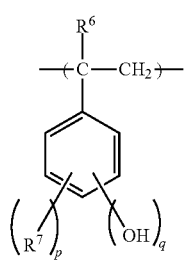
(4)

In the above formula (4), $R^6$ represents a hydrogen atom or a methyl group; $R^7$ represents a monovalent organic group having 1 to 20 carbon atoms; p is an integer of 0 to 3, wherein in a case in which $R^7$ is present in a plurality of number, a plurality of $R^7$s may be each identical or different; and q is an integer of 1 to 3, wherein a sum of p and q is no greater than 5.

In light of the copolymerizability of a monomer that gives the structural unit (III), $R^6$ preferably represents a hydrogen atom.

Examples of the monovalent organic group having 1 to 20 carbon atoms represented by $R^7$ include monovalent organic groups similar to those exemplified in connection with the monovalent organic group represented by $R^a$, $R^b$, $R^{5a}$ or $R^{5b}$ in the structural unit (II-2), and the like. Of these, monovalent chain hydrocarbon groups are preferred, alkyl groups are more preferred, and a methyl group is still more preferred.

Preferably, p is an integer of 0 to 2, more preferably 0 or 1, and still more preferably 0.

Preferably, q is 1 or 2, and more preferably 1.

Examples of the structural unit (III) include structural units represented by the following formulae (4-1) to (4-4), and the like.

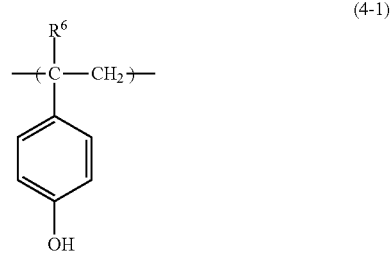
(4-1)

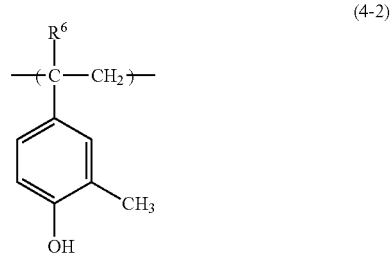
(4-2)

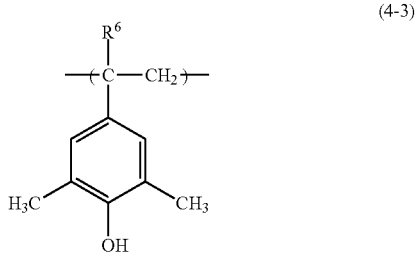
(4-3)

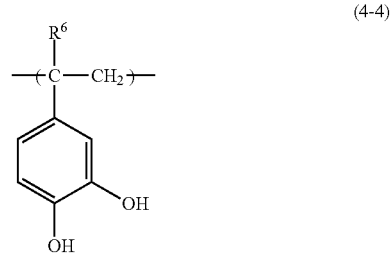
(4-4)

In the above formulae (4-1) to (4-4), $R^6$ is as defined in the above formula (4).

Of these, the structural units represented by the above formulae (4-1) and (4-2) are preferred, and the structural unit represented by the above formula (4-1) is more preferred.

The proportion of the structural unit (III) is preferably 0 mol % to 90 mol %, more preferably 30 mol % to 80 mol %, and still more preferably 50 mol % to 75 mol % with respect to the total structural units constituting the polymer (A). When the proportion of the structural unit (III) falls within the above range, the sensitivity of the radiation-sensitive resin composition can be further improved.

It is to be noted that the structural unit (III) can be formed by polymerizing a monomer obtained from hydroxystyrene by substitution of the hydrogen atom of an —OH group thereof with a t-butyl group or the like, and thereafter subjecting the obtained polymer to a hydrolysis reaction in the presence of an amine, or the like.

Other Structural Unit

The polymer (A) may have a structural unit other than the structural units (I) to (III). The other structural unit is exemplified by a structural unit derived from a (meth)acrylic acid ester that includes a nonlabile monovalent alicyclic hydrocarbon group, and the like. The proportion of the other structural unit is preferably no greater than 20 mol %, and more preferably no greater than 10 mol % with respect to the total structural units constituting the polymer (A).

Synthesis Method of Polymer (A)

The polymer (A) can be synthesized by a common method such as radical polymerization or the like. For example, the polymer (A) is preferably synthesized by: (1) a method including adding a solution containing a monomer and a radical initiator dropwise to a solution containing a reaction solvent or a monomer to permit a polymerization reaction; (2) a method including separately adding a solution containing a monomer and a solution containing a radical initiator dropwise to a solution containing a reaction solvent or a monomer to permit a polymerization reaction; (3) a method including separately adding a plurality of kinds of solutions containing each monomer, and a solution containing a radical initiator dropwise to a solution containing a reaction solvent or a monomer to permit a polymerization reaction; and (4) a method of permitting a polymerization reaction of a solution containing a monomer and a radical initiator in the absence of a solvent or in a reaction solvent; or the like.

It is to be noted that in a case where the reaction is permitted through adding a monomer solution to another monomer solution dropwise, the amount of the monomer in the monomer solution added dropwise is preferably no less than 30 mol %, more preferably no less than 50 mol %, and still more preferably no less than 70 mol % with respect to the total amount of the monomer used in the polymerization.

The reaction temperature in these methods may be appropriately predetermined in accordance with the initiator species. The reaction temperature is typically 30° C. to 150° C., preferably 40° C. to 150° C., and more preferably 50° C. to 140° C. The time period of the dropwise addition may vary depending on conditions such as the reaction temperature, the initiator type and the monomer to be reacted and the like, and is typically 30 min to 8 hrs, preferably 45 min to 6 hrs, and more preferably 1 hour to 5 hrs. In addition, although the total reaction time period including the time period of the dropwise addition may also vary depending on conditions similarly to the time period of the dropwise addition, the total reaction time period is typically 30 min to 12 hrs, preferably 45 min to 12 hrs, and more preferably 1 to 10 hrs.

Examples of the radical initiator for use in the polymerization include: azo radical initiators such as azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile), dimethyl 2,2'-azobis(2-methylpropionate) and dimethyl 2,2'-azobisisobutyrate; peroxide radical initiators such as benzoyl peroxide, t-butyl hydroperoxide and cumene hydroperoxide; and the like. Of these, AIBN and dimethyl 2,2'-azobis(2-methylpropionate) are preferred. It is to be noted that the radical initiator may be used either alone or in combination of two or more types thereof.

Any solvent can be used as the reaction solvent as long as the solvent can dissolve the monomer, and is other than solvents that inhibit polymerization (nitrobenzene having a polymerization inhibitory effect, a mercapto compound having a chain transfer effect, etc.). Examples of the reaction solvent include alcohols, ethers, ketones, amides, esters, lactones, nitriles, mixed solvents of these, and the like. These solvents may be used either alone or in combination of two or more types thereof.

The polymer obtained by the polymerization reaction is preferably recovered by a reprecipitation technique. More specifically, after the completion of the polymerization reaction, the intended polymer is recovered in the form of powder through charging the polymerization mixture into a reprecipitation solvent. Alcohols, alkanes and the like may be used as the reprecipitation solvent, either alone or in combination of two or more types thereof. Moreover, in addition to the reprecipitation technique, a liquid separating operation, a column operation, an ultrafiltration operation or the like enables the polymer to be recovered through eliminating low molecular weight components such as monomers and oligomers.

The polystyrene equivalent weight average molecular weight (Mw) of the polymer (A) as determined by gel permeation chromatography (GPC) is preferably 1,000 to 50,000, more preferably 2,000 to 40,000, still more preferably 3,000 to 30,000, and particularly preferably 5,000 to 20,000. When the Mw of the polymer (A) is less than the lower limit, the heat resistance of the resist pattern formed from the radiation-sensitive resin composition may be deteriorated. When the Mw of the polymer (A) is greater than the upper limit, the developability of the radiation-sensitive resin composition may be deteriorated.

The ratio (Mw/Mn, or dispersity index) of the Mw to the polystyrene equivalent number average molecular weight (Mn), as determined by GPC, of the polymer (A) is preferably 1 to 5, more preferably 1 to 3, and still more preferably 1 to 2.5.

The content of the polymer (A) is preferably no less than 70% by mass, more preferably no less than 80% by mass, and still more preferably no less than 85% by mass with respect to the total solid content in the radiation-sensitive resin composition.

(B) Compound

The compound (B) is represented by the following formula (1). Due to containing the compound (B), the radiation-sensitive resin composition exhibits superior LWR performance, resolution, rectangularity of a cross-sectional shape, and depth of focus. Although not necessarily clarified, the reason for achieving the effects described above due to the radiation-sensitive resin composition containing the compound (B) is presumed, for example, as in the following. Specifically, the compound (B) includes a carbonyl group adjacent to a carboxylate anion. Due to the presence of this carbonyl group, the polarity of the compound (B) would be increased more properly, and the basicity of the carboxylate anion would be decreased properly. Accordingly, acid trap performances of the compound (B) as an acid diffusion control agent in the resist film would be controlled more properly, and additionally, migration of the compound (B) itself by diffusion in the resist film would be inhibited. Therefore, consequently, the LWR performance, the resolution, the rectangularity of the cross-sectional shape, and the depth of focus of the radiation-sensitive resin composition can be improved.

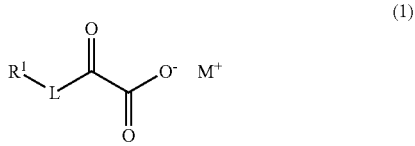

(1)

In the above formula (1), R¹ represents a monovalent organic group having 1 to 30 carbon atoms; L represents a single bond, an oxygen atom or a sulfur atom; and M⁺ represents a monovalent radioactive ray-labile onium cation.

The monovalent organic group having 1 to 30 carbon atoms represented by R¹ is exemplified by: a monovalent hydrocarbon group having 1 to 30 carbon atoms; a hetero atom-containing group obtained from the hydrocarbon group by incorporating a hetero atom-having group between adjacent two carbons thereof; a group obtained from the hydrocarbon group or the hetero atom-containing group by substituting a part or all of hydrogen atoms included therein with a substituent; and the like.

The monovalent hydrocarbon group having 1 to 30 carbon atoms is exemplified by a monovalent chain hydrocarbon group having 1 to 30 carbon atoms, a monovalent alicyclic hydrocarbon group having 3 to 30 carbon atoms, a monovalent aromatic hydrocarbon group having 6 to 30 carbon atoms; and the like.

Examples of the chain hydrocarbon group include:

alkyl groups such as a methyl group, an ethyl group, a n-propyl group, an i-propyl group, a n-butyl group, an i-butyl group, a sec-butyl group and a t-butyl group;

alkenyl groups such as an ethenyl group, a propenyl group, a butenyl group, a pentenyl group, a hexenyl group, an octenyl group and a decenyl group;

alkynyl groups such as an ethynyl group, a propynyl group, a butynyl group, a pentynyl group, a hexynyl group and an octynyl group; and the like.

Examples of the alicyclic hydrocarbon group include:

monocyclic cycloalkyl groups such as a cyclopropyl group, a cyclobutyl group, a cyclopentyl group, a cyclohexyl group, a cyclooctyl group and a cyclodecyl group;

polycyclic cycloalkyl groups such as a norbornyl group, an adamantyl group, a tricyclodecyl group and a tetracyclododecyl group;

monocyclic cycloalkenyl groups such as a cyclopropenyl group, a cyclobutenyl group, a cyclopentenyl group, a cyclohexenyl group, a cyclooctenyl group and a cyclodecenyl group;

polycyclic cycloalkenyl groups such as a norbornenyl group, a tricyclodecenyl group and a tetracyclododecenyl group; and the like.

Examples of the aromatic hydrocarbon group include:

aryl groups such as a phenyl group, a tolyl group, a xylyl group, a naphthyl group and an anthryl group;

aralkyl groups such as a benzyl group, a phenethyl group, a naphthylmethyl group and an anthrylmethyl group; and the like.

Example of the hetero atom in the hetero atom-having group include an oxygen atom, a sulfur atom, a nitrogen atom, a phosphorus atom, a silicon atom, and the like.

Examples of the hetero atom-having group include —O—, —CO—, —NR″—, —S—, —CS—, a combination of two or more thereof, and the like, wherein R″ represents a hydrogen atom or a monovalent hydrocarbon group having 1 to 20 carbon atoms.

Examples of the substituent include: halogen atoms such as a fluorine atom, a chlorine atom, a bromine atom and an iodine atom; a hydroxy group; a nitro group; a cyano group; a sulfanyl group; an amino group; and the like.

Preferably, L represents a single bond or an oxygen atom.

In a case where L represents a single bond, R¹ represents preferably a monovalent hydrocarbon group or a monovalent fluorinated hydrocarbon group, more preferably an alkyl group, a cycloalkyl group, an aryl group or a fluorinated aryl group, still more preferably a tertiary alkyl group, a polycyclic cycloalkyl group, a substituted or unsubstituted phenyl group or a fluorinated alkyl-substituted phenyl group, particularly preferably a t-butyl group, an adamantyl group, a phenyl group or a di(trifluoromethyl)phenyl group, further particularly preferably an adamantyl group, a phenyl group or a di(trifluoromethyl)phenyl group. When R¹ represents any of the above groups in the case of L representing the single bond, the basicity of the compound (B) for use as an acid diffusion control agent can be regulated more properly, and the bulkiness of R¹ can be increased, and consequently, the LWR performance, the resolution, the rectangularity of the cross-sectional shape, and the depth of focus of the radiation-sensitive resin composition can be further improved. In addition, such a compound (B) can be produced conveniently from an easily-available basic ingredient.

In a case where L represents an oxygen atom or a sulfur atom, R¹ represents preferably a monovalent hydrocarbon group, a monovalent fluorinated hydrocarbon group, a monovalent aliphatic heterocyclic group or a monovalent fluorinated aliphatic heterocyclic group, more preferably a monovalent alicyclic hydrocarbon group, a monovalent aromatic hydrocarbon group, a monovalent fluorinated chain hydrocarbon group or a monovalent aliphatic heterocyclic group, still more preferably an aryl group, a fluorinated alkyl group, a group that includes lactone structure, a group that includes sultone structure, and particularly preferably a phenyl group, a 1,1,1,3,3,3-hexafluoropropan-2-yl group, a 5-oxo-4-oxatricyclo[4.3.1.1$^{3,8}$]undecan-yl group, a norbornanelacton-2-yl group, a norbornanesulton-2-yl group. When R¹ represents any of the above groups in the case of L representing the oxygen atom or the sulfur atom, the polarity of the compound (B) for use as an acid diffusion control agent can be further increased, and additionally the bulkiness of R¹ can be further increased. Consequently, the LWR performance, the resolution, the rectangularity of the cross-sectional shape, and the depth of focus of the radiation-sensitive resin composition can be further improved. In addition, in the case of L representing the oxygen atom, it is also preferred that R¹ represents a monovalent acid-labile group, or a monovalent group that includes an acetal structure. When R¹ represents any of the above groups in the case of L representing the oxygen atom, the compound (B) has comparatively lower polarity before an exposure, leading to increased dispersibility thereof in the resist film, whereas after the exposure, a carboxy group, a hydroxy group or the like can be generated, leading to an increase in polarity. Consequently, the LWR performance, the resolution, the rectangularity of the cross-sectional shape, and the depth of focus of the radiation-sensitive resin composition can be further improved. The monovalent acid-labile group is preferably a tertiary alicyclic hydrocarbon group, more preferably a 1-alkyl-1-monocyclic cycloalkyl group or a 2-alkyl-2-polycyclic cycloalkyl group, and still more preferably a 1-i-propyl-1-cyclopentyl group, a 1-ethyl-1-cyclooctyl group or a 2-ethyl-2-adamantyl group. The monovalent group that includes an acetal structure is preferably a monovalent group that includes a cyclic acetal structure, and more preferably a monovalent group that includes a 2,2-hydrocarbon group-substituted-1,3-dioxacyclopentane structure.

Examples of the monovalent radioactive ray-labile onium cation represented by M⁺ include radioactive ray-labile onium cations that contain an element such as S, I, O, N, P, Cl, Br, F, As, Se, Sn, Sb, Te and Bi. Of these, sulfonium cations that contain S (sulfur) as the element, and iodonium cations that contain I (iodine) as the element are preferred, sulfonium cations are more preferred, and a cation represented by the following formula (X) is still more preferred.

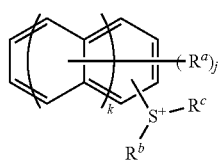
(X)

In the above formula (X), $R^a$ represents a fluorine atom, a hydroxy group, an alkyl group having 1 to 10 carbon atoms, an alkoxy group having 1 to 10 carbon atoms, an alkoxycarbonyl group having 2 to 11 carbon atoms or an alkylsulfonyl group having 1 to 10 carbon atoms; j is an integer of 0 to 9, wherein in a case where j is no less than 2, a plurality of $R^a$s may be each identical or different; $R^b$ and $R^c$ each independently represent a substituted or unsubstituted alkyl group having 1 to 10 carbon atoms, a substituted or unsubstituted aryl group having 6 to 20 carbon atoms, or $R^b$ and $R^c$ taken together represent a ring structure having 4 to 10 ring atoms together with the sulfur atom to which $R^b$ and $R^c$ bond; and "k" is an integer of 0 to 2.

Examples of the alkyl group having 1 to 10 carbon atoms which may be represented by $R^a$ include a methyl group, an ethyl group, a n-propyl group, an i-propyl group, a n-butyl group, an i-butyl group, a sec-butyl group, a t-butyl group, and the like.

Examples of the alkoxy group having 1 to 10 carbon atoms which may be represented by $R^a$ include a methoxy group, an ethoxy group, a n-propoxy group, an i-propoxy group, a n-butoxy group, an i-butoxy group, a sec-butoxy group, a t-butoxy group, and the like.

Examples of the alkoxycarbonyl group having 2 to 11 carbon atoms which may be represented by $R^a$ include a methoxycarbonyl group, an ethoxycarbonyl group, a n-propoxycarbonyl group, an i-propoxycarbonyl group, a n-butoxycarbonyl group, an i-butoxycarbonyl group, a sec-butoxycarbonyl group, a t-butoxycarbonyl group, and the like.

Examples of the alkylsulfonyl group having 1 to 10 carbon atoms which may be represented by $R^a$ include a methylsulfonyl group, an ethylsulfonyl group, a n-propylsulfonyl group, an i-propylsulfonyl group, a n-butylsulfonyl group, an i-butylsulfonyl group, a sec-butylsulfonyl group, a t-butylsulfonyl group, and the like.

$R^a$ represents preferably an alkyl group or an alkoxy group, and more preferably a methyl group, a t-butyl group, a methoxy group, a n-butoxy group or a t-butoxy group.

Preferably, j is an integer of 0 to 2, more preferably 0 or 1, and still more preferably 0.

Examples of the alkyl group having 1 to 10 carbon atoms which may be represented by $R^b$ or $R^c$ include alkyl groups similar to those exemplified in connection with the alkyl group which may be represented by $R^a$, and the like.

Examples of the aryl group having 6 to 20 carbon atoms which may be represented by $R^b$ or $R^c$ include a phenyl group, a tolyl group, a xylyl group, a mesityl group, a naphthyl group, a methylnaphthyl group, an anthryl group, a methylanthryl group, and the like.

Examples of the ring structure having 4 to 10 ring atoms which may be taken together represented by $R^b$ and $R^c$ together with the sulfur atom to which $R^b$ and $R^c$ bond include a thiophenium structure, a dihydrothiophenium structure, a tetrahydrothiophenium structure, a benzothiophenium structure, a dibenzothiophenium structure, and the like.

Preferably, "k" is 0 or 1, and more preferably 0.

Examples of the cation represented by the above formula (X) include cations represented by the following formulae (i-1) to (i-13), and the like.

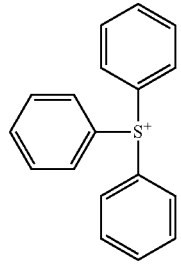
(i-1)

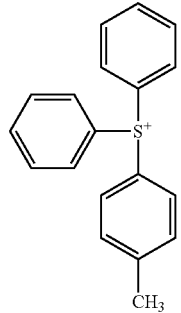
(i-2)

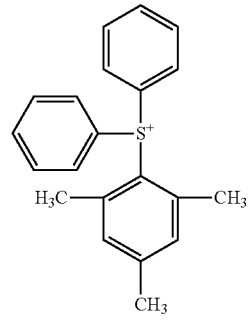
(i-3)

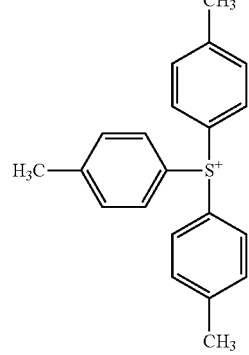
(i-4)

(i-5) 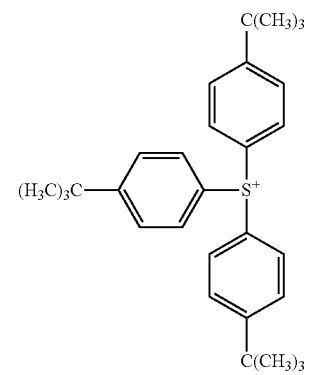
(i-6) 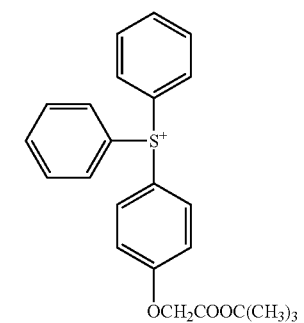
(i-7) 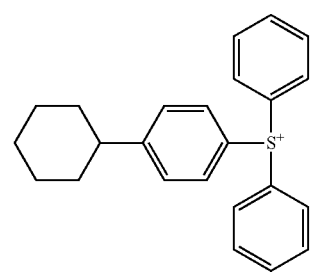
(i-8) 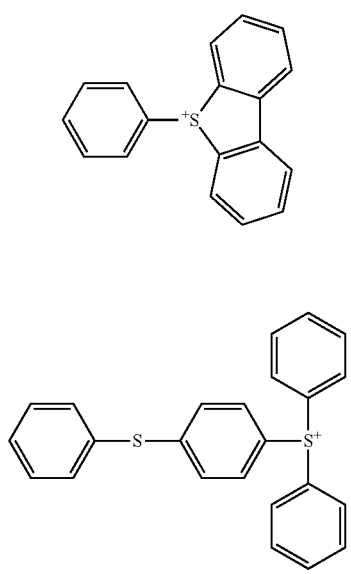
(i-9)
(i-10) 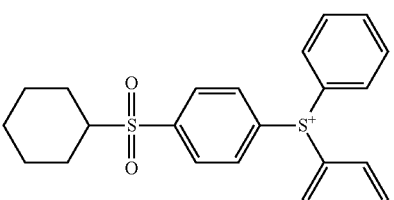
(i-11) 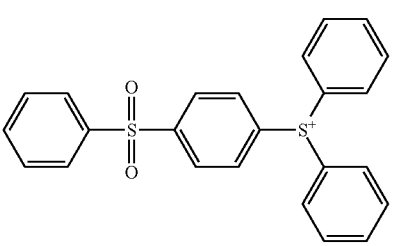
(i-12) 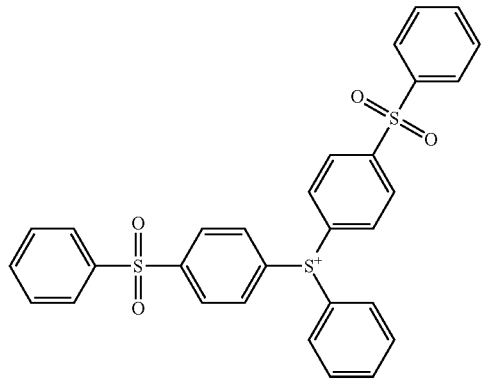
(i-13) 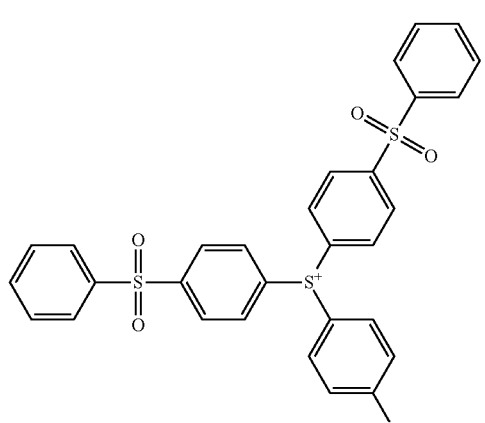
Of these, the cation represented by the above formula (i-1) is preferred.
When L represents a single bond, the compound (B) is exemplified by compounds represented by the following formulae (1-1-1) to (1-1-12) (hereinafter, may be also referred to as "compounds (1-1-1) to (1-1-12)"), and the like.

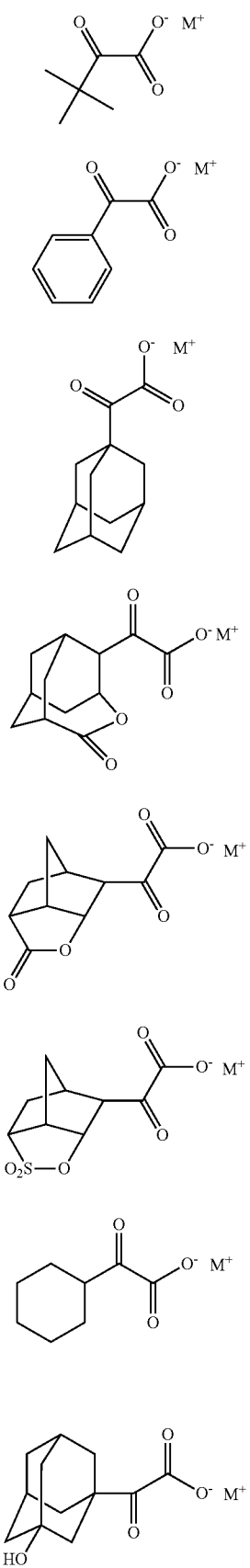
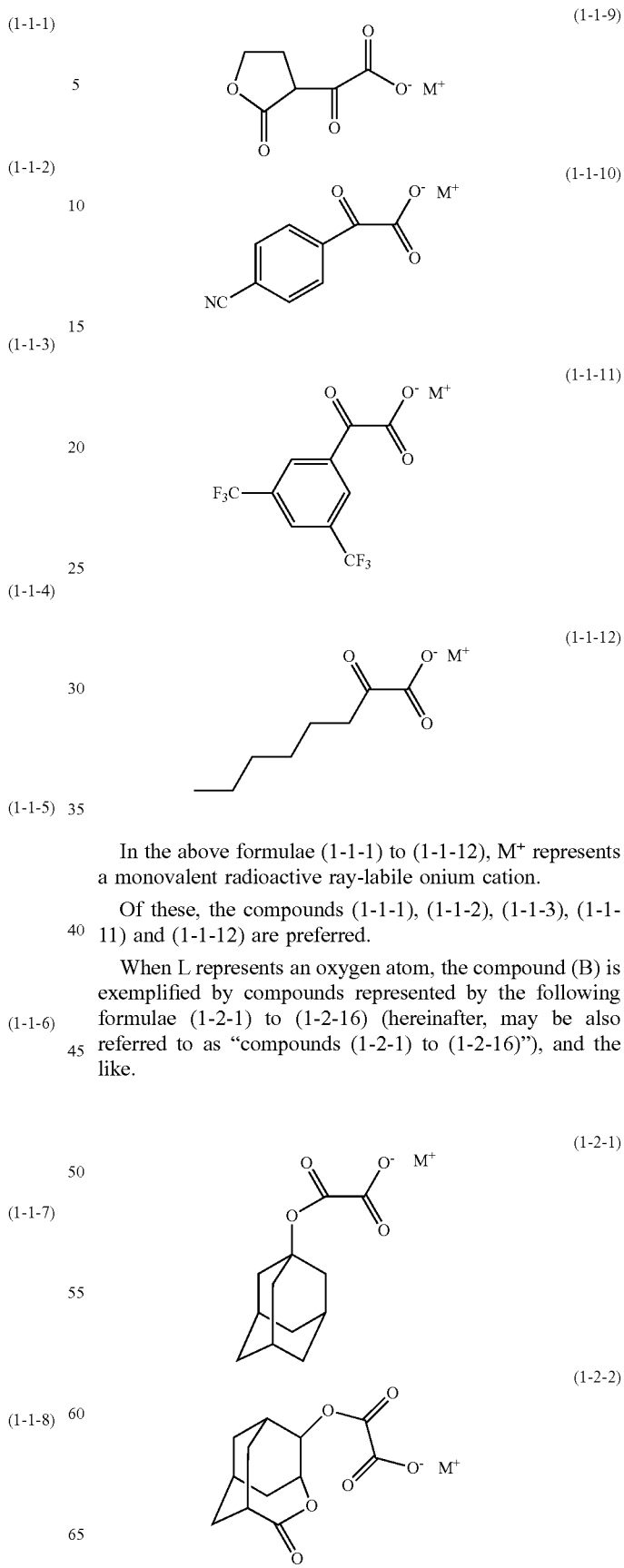
In the above formulae (1-1-1) to (1-1-12), M⁺ represents a monovalent radioactive ray-labile onium cation.
Of these, the compounds (1-1-1), (1-1-2), (1-1-3), (1-1-11) and (1-1-12) are preferred.
When L represents an oxygen atom, the compound (B) is exemplified by compounds represented by the following formulae (1-2-1) to (1-2-16) (hereinafter, may be also referred to as "compounds (1-2-1) to (1-2-16)"), and the like.

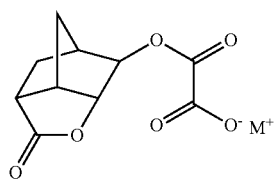 (1-2-3)
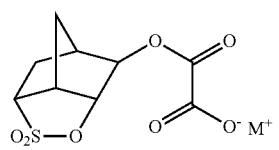 (1-2-4)
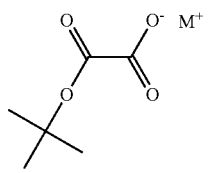 (1-2-5)
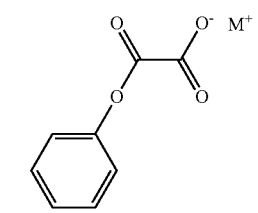 (1-2-6)
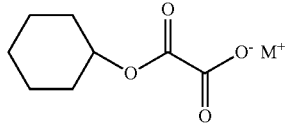 (1-2-7)
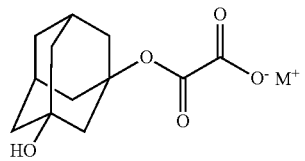 (1-2-8)
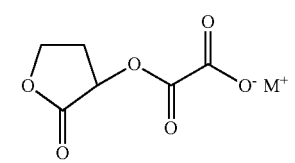 (1-2-9)
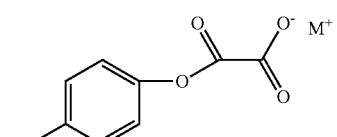 (1-2-10)
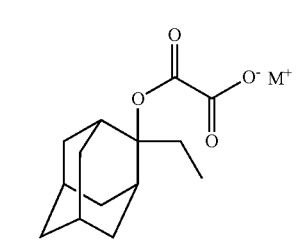 (1-2-11)
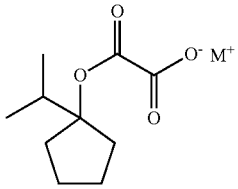 (1-2-12)
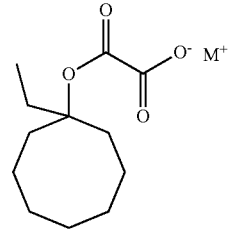 (1-2-13)
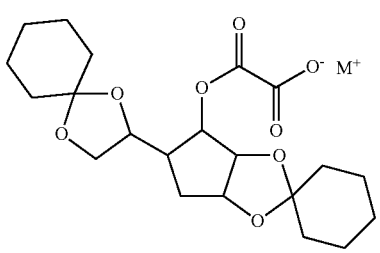 (1-2-14)
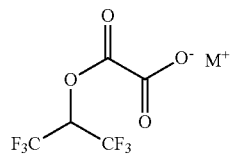 (1-2-15)
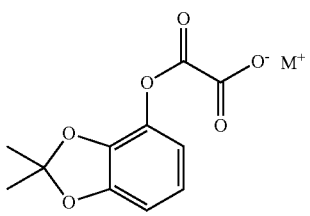 (1-2-16)
In the above formulae (1-2-1) to (1-2-16), $M^+$ represents a monovalent radioactive ray-labile onium cation.
Of these, the compounds (1-2-1) to (1-2-4) and (1-2-11) to (1-2-16) are preferred.
When L represents a sulfur atom, the compound (B) is exemplified by compounds represented by the following formulae (1-3-1) to (1-3-10) (hereinafter, may be also referred to as "compounds (1-3-1) to (1-3-10)"), and the like.
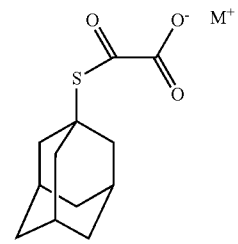 (1-3-1)

(1-3-2)
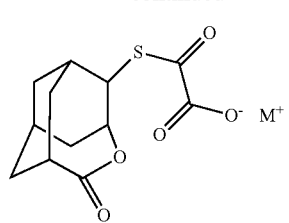

(1-3-3)
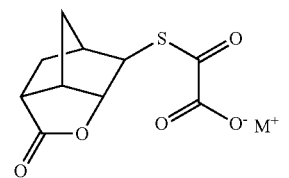

(1-3-4)
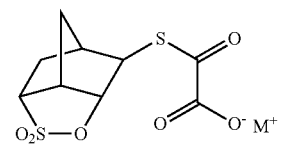

(1-3-5)
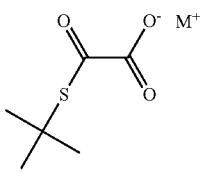

(1-3-6)
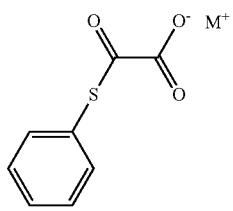

(1-3-7)
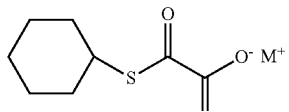

(1-3-8)
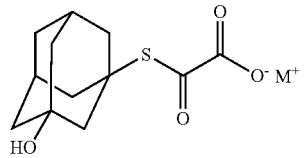

(1-3-9)
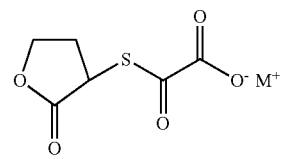

(1-3-10)
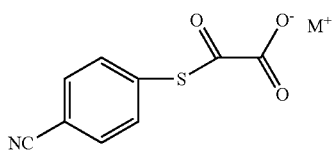

In the above formulae (1-3-1) to (1-3-10), M⁺ represents a monovalent radioactive ray-labile onium cation.

Of these, the compounds (1-3-1) to (1-3-4) and (1-3-6) are preferred, and the compound (1-3-6) is more preferred.

The compound (B) (i.e., the compound represented by the following formula (1)) can be produced conveniently in a favorable yield in accordance with the following reaction scheme, for example, by reacting a compound represented by the following formula (1a) (hereinafter, may be also referred to as "compound (1a)") with a compound represented by the following formula (1b) (hereinafter, may be also referred to as "compound (1b)").

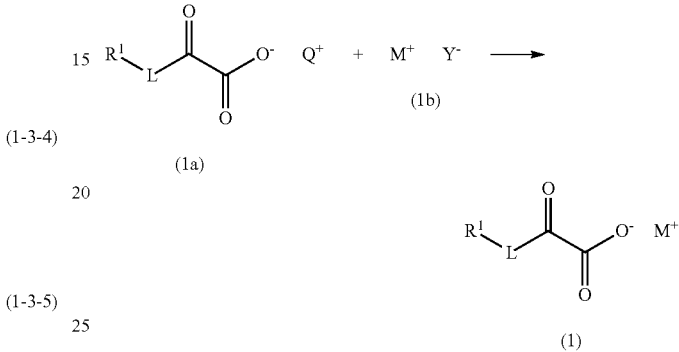

In the above formulae (1a), (1b) and (1), $R^1$ represents a monovalent organic group having 1 to 30 carbon atoms; L represents a single bond, an oxygen atom or a sulfur atom; $Q^+$ represents a monovalent alkali metal cation or a monovalent organic ammonium cation; $M^+$ represents a monovalent radioactive ray-labile onium cation; and $Y^-$ represents a monovalent halogen anion or a monovalent methylsulfuric acid anion.

The compound represented by the above formula (1) can be obtained by reacting the compound (1a) with the compound (1b) in a solvent such as a mixed solvent of dichloromethane and water, and thereafter subjecting the reaction product to an appropriate purification procedure such as column chromatography.

The compound (1a) can be obtained by reacting a corresponding carboxylic acid compound with an alkali metal hydroxide such as sodium hydroxide in a solvent such as a mixed solvent of tetrahydrofuran and water. Alternatively, when L represents an oxygen atom, the carboxylic acid compound can be obtained by reacting oxalic acid with an alcohol compound in a solvent such as dichloromethane in the presence of a base such as dimethylaminopyridine, and a dehydrating agent such as 1-ethyl-3-[3-(dimethylamino)propyl]carbodiimide, thereby executing partial esterification.

The lower limit of the content of the compound (B) is preferably 0.1 parts by mass, more preferably 0.3 parts by mass, still more preferably 0.5 parts by mass, and particularly preferably 1 part by mass with respect to 100 parts by mass of the polymer (A). The upper limit of the content of the compound (B) is preferably 30 parts by mass, more preferably 20 parts by mass, still more preferably 10 parts by mass, and particularly preferably 5 parts by mass with respect to 100 parts by mass of the polymer (A). When the content of the compound (B) falls within the above range, the radiation-sensitive resin composition can achieve a further improvement of the LWR performance, the resolution, the rectangularity of the cross-sectional shape, and the depth of focus.

(C) Acid Generator

The acid generator (C) is a substance that generates an acid upon an exposure. The acid generated from the acid generator (C), or the like allows the acid-labile group in the polymer (A) to be dissociated, thereby generating a carboxy group or the like. As a result, the solubility of the polymer (A) in a developer solution is altered. The acid generator (C) may be contained in the radiation-sensitive resin composition either in the form of a low molecular weight compound described later (hereinafter, may be also referred to as "(C) acid generating agent" or "acid generating agent (C)", as appropriate) or in the form incorporated as a part of the polymer, or in both of these forms.

The acid generating agent (C) is exemplified by an onium salt compound, an N-sulfonyloxyimide compound, a halogen-containing compound, a diazo ketone compound, and the like.

The onium salt compound is exemplified by a sulfonium salt, a tetrahydrothiophenium salt, an iodonium salt, a phosphonium salt, a diazonium salt, a pyridinium salt, and the like.

Examples of the sulfonium salt include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, triphenylsulfonium 2-bicyclo[2.2.1]hept-2-yl-1,1-difluoroethanesulfonate, triphenylsulfonium 2-(adamantan-1-ylcarbonyloxy)-2,2,3,3,3-pentafluoropropanesulfonate, triphenylsulfonium camphorsulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-cyclohexylphenyldiphenylsulfonium camphorsulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, 4-methanesulfonylphenyldiphenylsulfonium camphorsulfonate, triphenylsulfonium 1,1,2,2-tetrafluoro-6-(1-adamantanecarbonyloxy)-hexane-1-sulfonate, and the like.

Examples of the tetrahydrothiophenium salt include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl) tetrahydrothiophenium 2-bicyclo[2.2.1]hept-2-yl-1,1,2,2-tetrafluoroethanesulfonate, 1-(4-n-butoxynaphthalen-1-yl) tetrahydrothiophenium camphorsulfonate, 1-(6-n-butoxynaphthalen-2-yl)tetrahydrothiophenium trifluoromethanesulfonate, 1-(6-n-butoxynaphthalen-2-yl) tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl) tetrahydrothiophenium 2-bicyclo[2.2.1]hept-2-yl-1,1,2,2-tetrafluoroethanesulfonate, 1-(6-n-butoxynaphthalen-2-yl) tetrahydrothiophenium camphorsulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1,1,2,2-tetrafluoroethanesulfonate, 1-(3,5-dimethyl-4-hydroxyphenyl)tetrahydrothiophenium camphorsulfonate, and the like.

Examples of the iodonium salt include diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, diphenyliodonium camphorsulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, bis(4-t-butylphenyl)iodonium camphorsulfonate, and the like.

Examples of the N-sulfonyloxyimide compound include N-(trifluoromethanesulfonyloxy)bicyclo[2.2.1]hept-5-ene-2,3-dicarboxyimide, N-(nonafluoro-n-butanesulfonyloxy) bicyclo[2.2.1]hept-5-ene-2,3-dicarboxyimide, N-(perfluoro-n-octanesulfonyloxy)bicyclo[2.2.1]hept-5-ene-2,3-dicarboxyimide, N-(2-bicyclo[2.2.1]hept-2-yl-1,1,2,2-tetrafluoroethanesulfonyloxy)bicyclo[2.2.1]hept-5-ene-2,3-dicarboxyimide, N-(2-(3-tetracyclo[4.4.0.1$^{2,5}$.1$^{7,10}$] dodecanyl)-1,1-difluoroethanesulfonyloxy)bicyclo[2.2.1] hept-5-ene-2,3-dicarboxyimide, N-(camphorsulfonyloxy) bicyclo[2.2.1]hept-5-ene-2,3-dicarboxyimide, and the like.

Of these, the acid generating agent (C) is preferably an onium salt compound, more preferably a sulfonium salt, still more preferably a triphenylsulfonium salt, and particularly preferably triphenylsulfonium 2-(adamantan-1-ylcarbonyloxy)-2,2,3,3,3-pentafluoropropanesulfonate.

In a case where the acid generator (C) is the acid generating agent (C), in light of ensuring the sensitivity and developability of the radiation-sensitive resin composition, the content of the acid generator (C) is preferably no less than 0.1 parts by mass and no greater than 30 parts by mass, more preferably no less than 0.5 parts by mass and no greater than 20 parts by mass, still more preferably no less than 1 part by mass and no greater than 15 parts by mass, and particularly preferably no less than 2 parts by mass and no greater than 12 parts by mass with respect to 100 parts by mass of the polymer (A). When the content of the acid generating agent (C) falls within the above range, the sensitivity and developability of the radiation-sensitive resin composition may be increased. Consequently, the LWR performance, the resolution, the rectangularity of the cross-sectional shape, and the depth of focus of the radiation-sensitive resin composition can be improved. Either one, or two or more types of the acid generator (C) may be used.

(D) Other Acid Diffusion Controller

The radiation-sensitive resin composition may contain (D) other acid diffusion controller which is other than the compound (B). The other acid diffusion controller (D) exerts the effect of controlling a diffusion phenomenon of the acid generated from the acid generator (C) or the like upon an exposure in the resist film, and suppressing unfavorable chemical reactions at a light-unexposed site. Moreover, the other acid diffusion controller (D) can suppress variation of line width of the resist pattern caused by variation of post-exposure time delay from the exposure until a development treatment, which enables the composition with superior process stability to be obtained. When the radiation-sensitive resin composition further contains the other acid diffusion controller (D), the LWR performance, the resolution, the rectangularity of a cross-sectional shape, and the depth of focus of the radiation-sensitive resin composition can be further improved. The other acid diffusion controller (D) may be contained in the radiation-sensitive resin composition in the form of a low molecular weight compound described later (hereinafter, may be also referred to as "(D) other acid diffusion control agent" or "other acid diffusion control agent (D)", as appropriate), or in the form incorporated as a part of the polymer, or in both of these forms. The radiation-sensitive resin composition may contain either one, or two or more types of the other acid diffusion controller (D).

The other acid diffusion controller (D) is exemplified by an amine compound, an amide group-containing compound, a urea compound, a nitrogen-containing heterocyclic compound, and the like.

Examples of the amine compound include: mono(cyclo)alkylamines; di(cyclo)alkylamines; tri(cyclo)alkylamines; substituted alkylanilines or derivatives thereof; ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis(1-(4-aminophenyl)-1-methylethyl)benzene, 1,3-bis(1-(4-aminophenyl)-1-methylethyl)benzene, bis(2-dimethylaminoethyl)ether, bis(2-diethylaminoethyl)ether, 1-(2-hydroxyethyl)-2-imidazolidinone, 2-quinoxalinol, N,N,N',N'-tetrakis(2-hydroxypropyl)ethylenediamine, and N,N,N',N'',N''-pentamethyldiethylenetriamine; and the like.

Examples of the amide group-containing compound include: N-t-butoxycarbonyl group-containing amino compounds such as N-t-butoxycarbonyl-4-hydroxypiperidine; N-t-amyloxycarbonyl group-containing amino compounds such as N-t-amyloxycarbonyl-4-hydroxypiperidine; formamide, N-methylformamide, N,N-dimethylformamide, acetamide, N-methylacetamide, N,N-dimethylacetamide, propionamide, benzamide, pyrrolidone, N-methylpyrrolidone, N-acetyl-1-adamantylamine and tris(2-hydroxyethyl)isocyanurate; and the like.

Examples of the urea compound include urea, methylurea, 1,1-dimethylurea, 1,3-dimethylurea, 1,1,3,3-tetramethylurea, 1,3-diphenylurea, tri-n-butylthiourea, and the like.

Examples of the nitrogen-containing heterocyclic compound include: imidazoles such as 2-phenylimidazole; pyridines; piperazines; pyrazine, pyrazole, pyridazine, quinoxaline, purine, pyrrolidine, piperidine, piperidine ethanol, 3-piperidino-1,2-propanediol, morpholine, 4-methylmorpholine, 1-(4-morpholinyl)ethanol, 4-acetylmorpholine, 3-(N-morpholino)-1,2-propanediol, 1,4-dimethylpiperazine and 1,4-diazabicyclo[2.2.2]octane; and the like.

Of these, an amide group-containing compound is preferred, an N-t-butoxycarbonyl group-containing amino compound is more preferred, and N-t-butoxycarbonyl-4-hydroxypiperidine is still more preferred.

In addition, as the other acid diffusion controller (D), a photodegradable base which is sensitized upon an exposure to generate a weak acid can also be used. The photodegradable base is exemplified by an onium salt compound and the like that lose acid diffusion controllability through degradation upon an exposure (except for those corresponding to the compound (B)). Examples of the onium salt compound include a sulfonium salt compound represented by the following formula (5-1), an iodonium salt compound represented by the following formula (5-2), and the like.

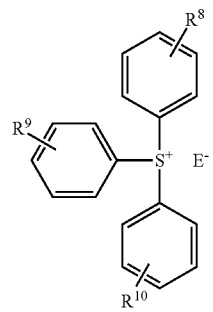

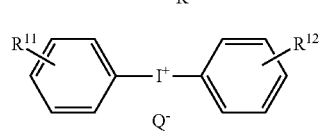

In the above formulae (5-1) and (5-2), $R^8$ to $R^{12}$ each independently represent a hydrogen atom, an alkyl group, an alkoxy group, a hydroxy group or a halogen atom; and $E^-$ and $Q^-$ each independently represent $OH^-$, $R^\beta$—$COO^-$, $R^\beta$—$SO_3^-$ or an anion represented by the following formula (5-3), wherein $R^\beta$ represents an alkyl group, an aryl group or an aralkyl group.

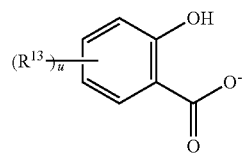

In the above formula (5-3), $R^{13}$ represents a linear or branched alkyl group having 1 to 12 carbon atoms or a linear or branched alkoxy group having 1 to 12 carbon atoms, wherein a part or all of hydrogen atoms included in the linear or branched alkyl group or the linear or branched alkoxyl group may be substituted with a fluorine atom; and u is an integer of 0 to 2.

Examples of the photodegradable base include compounds represented by the following formulae, and the like.

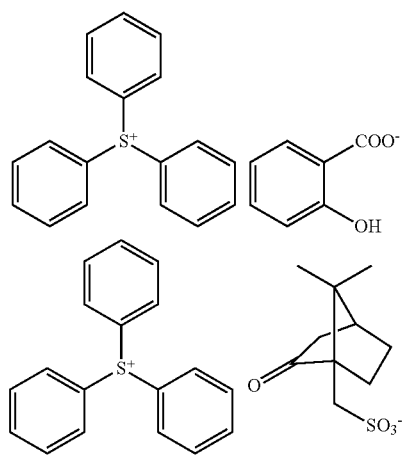

-continued

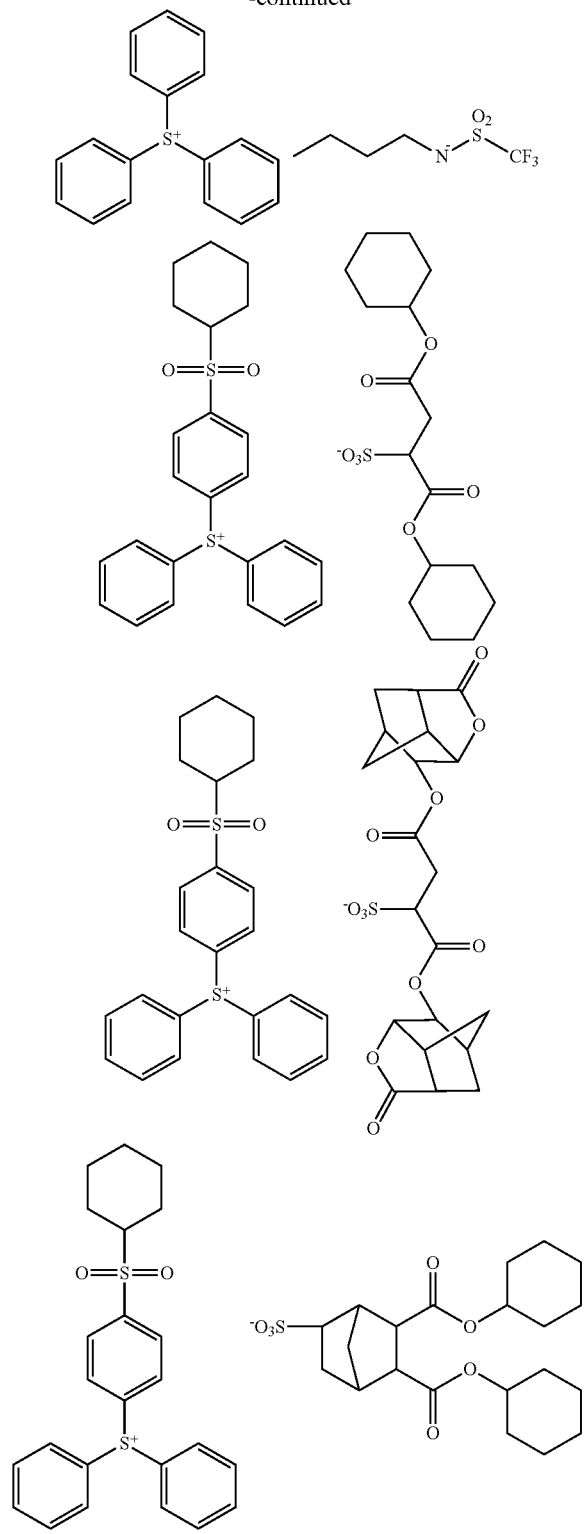

In the case of the other acid diffusion controller (D) being (D) an acid diffusion control agent, the content of the other acid diffusion controller (D) is preferably no greater than 30 parts by mass, more preferably 0.1 parts by mass to 20 parts by mass, and still more preferably 0.5 parts by mass to 10 parts by mass with respect to 100 parts by mass of the polymer (A). When the content of the other acid diffusion control agent (D) falls within the above range, the LWR performance and the like of the radiation-sensitive resin composition can be further improved.

(E) Polymer

The polymer (E) is a fluorine atom-containing polymer. When the radiation-sensitive resin composition further contains the polymer (E) in addition to the polymer (A), the polymer (E) may be unevenly distributed on the surface layer of the formed resist film, and consequently the hydrophobicity of the surface of the resist film can be increased. Thus, when liquid immersion lithography is executed, and the like, a superior inhibitory effect on elution of a substance from the resist film can be exhibited, and a sufficiently great receding contact angle of a liquid immersion liquid on the resist film can be attained, thereby enabling a higher-speed scanning.

The polymer (E) is not particularly limited as long as the polymer (E) contains a fluorine atom, and the polymer (E) is exemplified by: (1) a polymer that is per se insoluble in a developer solution, and becomes alkali-soluble by the action of an acid; (2) a polymer that is per se soluble in a developer solution, and enhances its alkali-solubility by the action of an acid; (3) a polymer that is per se insoluble in a developer solution, and becomes alkali-soluble by the action of an alkali; (4) a polymer that is per se soluble in a developer solution, and enhances its alkali-solubility by the action of an alkali; and the like.

Examples of the structure of the polymer (E) include:

a structure in which a fluorinated alkyl group bonds to the main chain of the polymer (E);

a structure in which a fluorinated alkyl group bonds to a side chain of the polymer (E);

a structure in which fluorinated alkyl groups bond to the main chain and a side chain; and the like.

Examples of the monomer that gives the structure in which a fluorinated alkyl group bonds to the main chain of the polymer (E) include: α-trifluoromethylacrylate compounds; β-trifluoromethylacrylate compounds; α,β-trifluoromethylacrylate compounds; compounds in which one or more vinylic hydrogen atoms are substituted with a fluorinated alkyl group such as a trifluoromethyl group; and the like.

Examples of the monomer that gives the structure in which a fluorinated alkyl group bonds to a side chain of the polymer (E) include: alicyclic olefin compounds such as norbornene which include a fluorinated alkyl group or a derivative thereof as a side chain; ester compounds of acrylic acid or methacrylic acid which include a fluorinated alkyl group or a derivative thereof as a side chain; one or more types of olefins having a fluorinated alkyl group or a derivative thereof as a side chain (i.e., a moiety excluding a double bond); and the like.

Examples of the monomer that gives the structure in which fluorinated alkyl groups bond to the main chain and a side chain include: ester compounds of α-trifluoromethylacrylic acid, β-trifluoromethylacrylic acid, α,β-trifluoromethylacrylic acid or the like which have a fluorinated alkyl group or a derivative thereof as a side chain; compounds which are obtained by substituting one or more vinylic hydrogen atoms with a fluorinated alkyl group such as a trifluoromethyl group and have a fluorinated alkyl group or a derivative thereof on a side chain thereof; compounds that are obtained from one or more types of alicyclic olefin compounds by substituting a hydrogen atom bonding to a double bond thereof with a fluorinated alkyl group such as a trifluoromethyl group and have a fluorinated alkyl group or a derivative thereof on a side chain thereof; and the like. It is to be noted that the alicyclic olefin compound as referred to means a compound that includes a double bond as a part of its ring.

The polymer (E) preferably has a structural unit (f1) represented by the following formula (6) and/or a structural unit (f2) represented by the following formula (7). In addition, the polymer (E) may have "other structural unit" excluding the structural units (f1) and (f2). It is to be noted that the polymer (E) may have one, or two or more types of each structural unit. Hereinafter, each structural unit is described in detail.

Structural Unit (f1)

The structural unit (f1) is represented by the following formula (6).

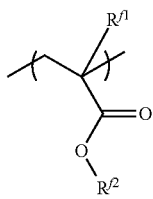

(6)

In the above formula (6), $R^{f1}$ represents a hydrogen atom, a fluorine atom, a methyl group or a trifluoromethyl group; $R^{f2}$ represents a linear or branched alkyl group having 1 to 6 carbon atoms and having a fluorine atom, or a monovalent alicyclic hydrocarbon group having 4 to 20 carbon atoms and having a fluorine atom, wherein a part or all of hydrogen atoms included in the alkyl group or the alicyclic hydrocarbon group may be substituted.

Examples of the linear or branched alkyl group having 1 to 6 carbon atoms include a methyl group, an ethyl group, a propyl group, a butyl group, and the like.

Examples of the monovalent alicyclic hydrocarbon group having 4 to 20 carbon atoms include a cyclopentyl group, a cyclopentylpropyl group, a cyclohexyl group, a cyclohexylmethyl group, a cycloheptyl group, a cyclooctyl group, a cyclooctylmethyl group, and the like.

Examples of the monomer that gives the structural unit (f1) include trifluoromethyl(meth)acrylate, 2,2,2-trifluoroethyl(meth)acrylate, perfluoroethyl(meth)acrylate, perfluoro-n-propyl(meth)acrylate, perfluoro-i-propyl(meth) acrylate, perfluoro-n-butyl (meth)acrylate, perfluoro-i-butyl (meth)acrylate, perfluoro-t-butyl (meth)acrylate, perfluorocyclohexyl(meth)acrylate, 2-(1,1,1,3,3,3-hexafluoro)propyl (meth)acrylate, 1-(2,2,3,3,4,4,5,5-octafluoro)pentyl(meth)acrylate, 1-(2,2,3,3,4,4,5,5-octafluoro) hexyl(meth)acrylate, perfluorocyclohexylmethyl(meth) acrylate, 1-(2,2,3,3,3-pentafluoro)propyl(meth)acrylate, 1-(2,2,3,3,4,4,4-heptafluoro)butyl(meth)acrylate, 1-(3,3,4,4, 5,5,6,6,7,7,8,8,9,9,10,10,10-heptadecafluoro)decyl(meth) acrylate, 1-(5-trifluoromethyl-3,3,4,4,5,6,6,6-octafluoro) hexyl(meth)acrylate, and the like.

Structural units represented by the following formulae (6-1) and (6-2) are preferred as the structural unit (f1).

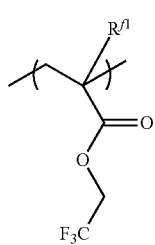

(6-1)

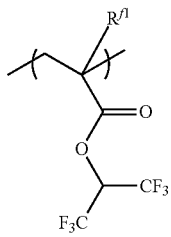

(6-2)

In the above formulae (6-1) and (6-2), $R^{f1}$ is as defined in the above formula (6).

Of these, the structural unit represented by the formula (6-1) is more preferred.

The proportion of the structural unit (f1) is preferably 10 mol % to 70 mol %, and more preferably 20 mol % to 50 mol % with respect to the total structural units constituting the polymer (E).

Structural Unit (f2)

The structural unit (f2) is represented by the following formula (7).

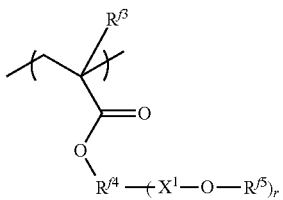

(7)

In the above formula (7), $R^{f3}$ represents a hydrogen atom, a fluorine atom, a methyl group, or a trifluoromethyl group; $R^{f4}$ represents a linking group having a valency of (r+1); $X^1$ represents a divalent linking group having a fluorine atom; $R^{f5}$ represents a hydrogen atom or a monovalent organic group; and "r" is an integer of 1 to 3, wherein in a case where "r" is 2 or 3, a plurality of $X^1$s may be each identical or different, and a plurality of $R^{f5}$s may be each identical or different.

In the above formula (7), the linking group having a valency of (r+1) which is represented by $R^{f4}$ is exemplified by a linear or branched hydrocarbon group having 1 to 30 carbon atoms, an alicyclic hydrocarbon group having 3 to 30 carbon atoms, an aromatic hydrocarbon group having 6 to 30 carbon atoms, or a group obtained by combining any of these groups with at least one selected from the group consisting of an oxygen atom, a sulfur atom, an ether group, an ester group, a carbonyl group, an imino group and an amide group; and the like. In addition, the linking group having a valency of (r+1) may have a substituent.

Examples of the linear or branched hydrocarbon group having 1 to 30 carbon atoms include groups obtained from a hydrocarbon group such as methane, ethane, propane, butane, pentane, hexane, heptane, decane, icosane or triacontane by eliminating (r+1) hydrogen atoms therefrom, and the like.

Examples of the alicyclic hydrocarbon group having 3 to 30 carbon atoms include groups obtained from the following hydrocarbon by eliminating (r+1) hydrogen atoms therefrom:

a monocyclic saturated hydrocarbon such as cyclopropane, cyclobutane, cyclopentane, cyclohexane, cycloheptane, cyclooctane, cyclodecane, methylcyclohexane or ethylcyclohexane;

a monocyclic unsaturated hydrocarbon such as cyclobutene, cyclopentene, cyclohexene, cycloheptene, cyclooctene, cyclodecene, cyclopentadiene, cyclohexadiene, cyclooctadiene or cyclodecadiene;

a polycyclic saturated hydrocarbon such as bicyclo[2.2.1]heptane, bicyclo[2.2.2]octane, tricyclo[5.2.1.0$^{2,6}$]decane, tricyclo[3.3.1.1$^{3,7}$]decane, tetracyclo[6.2.1.1$^{3,6}$.0$^{2,7}$]dodecane or adamantane;

a polycyclic unsaturated hydrocarbon such as bicyclo[2.2.1]heptene, bicyclo[2.2.2]octene, tricyclo[5.2.1.0$^{2,6}$]decene, tricyclo[3.3.1.1$^{3,7}$]decene or tetracyclo[6.2.1.1$^{3,6}$.0$^{2,7}$]dodecene; and the like.

Examples of the aromatic hydrocarbon group having 6 to 30 carbon atoms include groups obtained by eliminating (r+1) hydrogen atoms from an aromatic hydrocarbon group such as benzene, naphthalene, phenanthrene, anthracene, tetracene, pentacene, pyrene, picene, toluene, xylene, ethylbenzene, mesitylene or cumene, and the like.

In the above formula (7), the divalent linking group having a fluorine atom represented by $X^1$ is exemplified by a divalent linear hydrocarbon group having 1 to 20 carbon atoms and having a fluorine atom. $X^1$ is exemplified by groups represented by the following formulae (X1-1) to (X1-6); and the like.

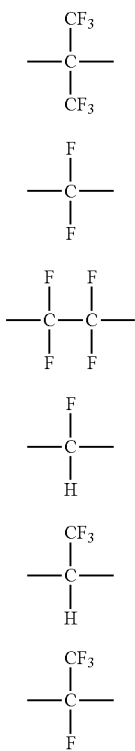

$X^1$ is preferably the group represented by the above formula (X1-1) or (X1-2), and more preferably the group represented by the formula (X1-2).

Examples of the monovalent organic group represented by $R^{f5}$ in the above formula (7) include: linear or branched hydrocarbon groups having 1 to 30 carbon atoms; alicyclic hydrocarbon groups having 3 to 30 carbon atoms; aromatic hydrocarbon groups having 6 to 30 carbon atoms; groups obtained by combining any of these groups with at least one selected from the group consisting of an oxygen atom, a sulfur atom, an ether group, an ester group, a carbonyl group, an imino group and an amide group; and the like.

Examples of the structural unit (f2) include structural units represented by the following formulae (7-1) and (7-2), and the like.

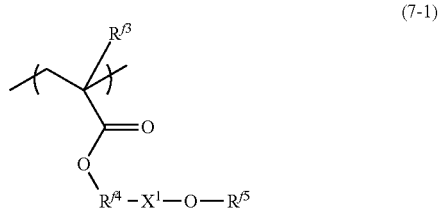

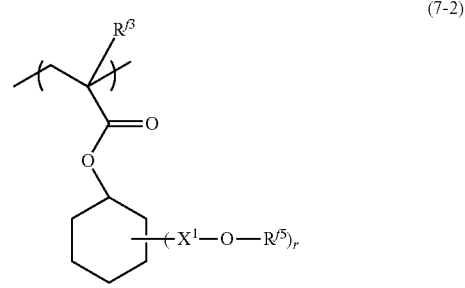

In the above formula (7-1), $R^{f4}$ represents a divalent linear, branched or cyclic saturated or unsaturated hydrocarbon group having 1 to 20 carbon atoms; and $R^{f3}$, $X^1$ and $R^{f5}$ are as defined in the above formula (7).

In the above formula (7-2), $R^{f3}$, $X^1$, $R^{f5}$ and "r" are as defined in the above formula (7), wherein in a case where "r" is 2 or 3, a plurality of $X^1$s may be each identical or different, and a plurality of $R^{f5}$s may be each identical or different.

Examples of the structural units represented by the above formulae (7-1) and (7-2) include structural units represented by the following formulae (7-1-1) to (7-1-3) and (7-2-1), and the like.

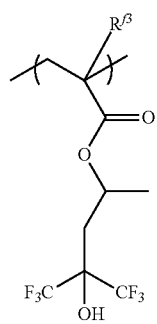

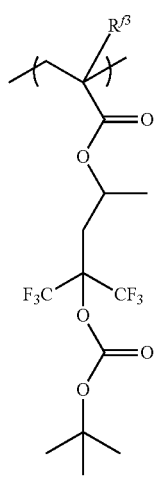

(7-1-2)

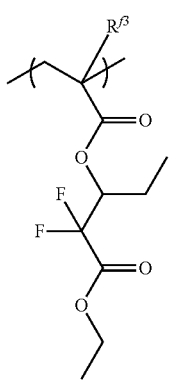

(7-1-3)

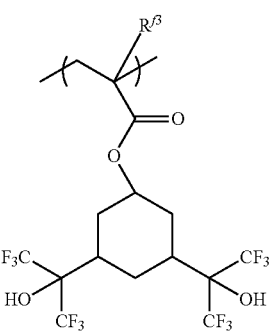

(7-2-1)

In the above formulae (7-1-1) to (7-1-3) and (7-2-1), $R^{\beta}$ is as defined in the above formula (7).

The structural unit (f2) is preferably the structural unit represented by the above formula (7-1), and more preferably the structural unit represented by the above formula (7-1-3).

Examples of the monomer that gives the structural unit (f2) include (meth)acrylic acid [2-(1-ethyloxycarbonyl-1,1-difluoro-n-butyl)] ester, (meth)acrylic acid (1,1,1-trifluoro-2-trifluoromethyl-2-hydroxy-3-propyl) ester, (meth)acrylic acid (1,1,1-trifluoro-2-trifluoromethyl-2-hydroxy-4-butyl) ester, (meth)acrylic acid (1,1,1-trifluoro-2-trifluoromethyl-2-hydroxy-5-pentyl) ester, (meth)acrylic acid 2-{[5-(1',1',1'-trifluoro-2'-trifluoromethyl-2'-hydroxy)propyl]bicyclo[2.2.1]heptyl} ester, and the like. Of these, (meth)acrylic acid [2-(1-ethyloxycarbonyl-1,1-difluoro-n-butyl)] ester is preferred.

The proportion of the structural unit (12) is preferably 30 mol % to 90 mol %, and more preferably 50 mol % to 80 mol % with respect to the total structural units constituting the polymer (E).

Other Structural Unit

The polymer (E) may have "other structural unit" excluding the structural units (f1) and (f2). The other structural unit is exemplified by the structural unit (I) of the polymer (A), and the like.

The proportion of the other structural unit is preferably 5 mol % to 90 mol %, more preferably 10 mol % to 80 mol %, and still more preferably 20 mol % to 70 mol % with respect to the total structural units constituting the polymer (E).

The content of the polymer (E) is preferably no greater than 20 parts by mass, more preferably 0.1 parts by mass to 15 parts by mass, still more preferably 1 part by mass to 10 parts by mass, and particularly preferably 1 part by mass to 6 parts by mass with respect to 100 parts by mass of the polymer (A). When the content of the polymer (E) is greater than the upper limit, the water repellency of the surface of the resist film may be so enhanced that a failure in development may occur.

The polymer (E) preferably has a percentage content of fluorine atoms greater than that of the polymer (A). When the polymer (E) has a greater percentage content of fluorine atoms than that of the polymer (A), the water repellency of the surface of the resist film formed from the radiation-sensitive resin composition containing the polymer (A) and the polymer (E) can be further enhanced. The difference between the percentage content of fluorine atoms of the polymer (E) and the percentage content of fluorine atoms of the polymer (A) is preferably no less than 1% by mass, and more preferably no less than 3% by mass.

Moreover, the percentage content of fluorine atoms of the polymer (E) is preferably no less than 1% by mass, more preferably no less than 3% by mass, still more preferably no less than 5% by mass, and particularly preferably no less than 10% by mass.

It is to be noted that the percentage content of fluorine atoms (% by mass) can be calculated based on the structure of the polymer determined by $^{13}$C-NMR spectroscopy.

Production Method of Polymer (E)

The polymer (E) can be produced, for example, by polymerizing monomer(s) corresponding to each given structural unit(s) in an appropriate solvent for polymerization with the use of a radical polymerization initiator.

Examples of the radical polymerization initiator include radical polymerization initiators similar to those exemplified in connection with the production method of the polymer (A), and the like. Examples of the solvent for polymerization include solvents for polymerization similar to those exemplified in connection with the production method of the polymer (A), and the like.

The reaction temperature in the polymerization is typically 40° C. to 150° C., and preferably 50° C. to 120° C. The reaction time period is typically 1 hour to 48 hrs, and preferably 1 hour to 24 hrs.

The Mw of the polymer (E) is preferably 1,000 to 50,000, more preferably 2,000 to 30,000, and still more preferably 3,000 to 10,000. When the Mw of the polymer (E) is less than 1,000, a sufficient receding contact angle cannot be attained. On the other hand, when the Mw is greater than 50,000, developability of the resulting resist tends to be deteriorated.

The ratio (Mw/Mn) of the Mw to the Mn of the polymer (E) is preferably 1 to 5, and more preferably 1 to 3.

(F) Solvent

The solvent (F) is a component for dissolving or dispersing the polymer (A), the compound (B) and the optional component. The solvent (F) is exemplified by an alcohol solvent, a ketone solvent, an amide solvent, an ether solvent, an ester solvent, and the like. The solvent (F) may be used either alone of one type, or in combination of two or more types thereof.

Examples of the alcohol solvent include:

monohydric alcohol solvents such as methanol, ethanol, n-propanol, iso-propanol, n-butanol, iso-butanol, sec-butanol, tert-butanol, n-pentanol, iso-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol and diacetone alcohol;

polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol and tripropylene glycol;

polyhydric alcohol partial ether solvents such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether and dipropylene glycol monopropyl ether; and the like.

Examples of the ketone solvent include:

chain ketone solvents such as acetone, methyl ethyl ketone, methyl n-propyl ketone, methyl n-butyl ketone, diethyl ketone, methyl iso-butyl ketone, methyl n-pentyl ketone, ethyl n-butyl ketone, methyl n-hexyl ketone, di-iso-butyl ketone, trimethylnonanone, 2,4-pentanedione, acetonylacetone, diacetone alcohol and acetophenone;

cyclic ketone solvents such as cyclopentanone, cyclohexanone, cycloheptanone, cyclooctanone and methylcyclohexanone; and the like.

Examples of the amide solvent include:

chain amide solvents such as N-methylformamide, N,N-dimethylformamide, N,N-diethylformamide, acetamide, N-methylacetamide, N,N-dimethylacetamide and N-methylpropionamide;

cyclic amide solvents such as N-methylpyrrolidone and N,N'-dimethylimidazolidinone; and the like.

Examples of the ether solvent include: chain ether solvents such as diethyl ether, dipropyl ether, dibutyl ether and diphenyl ether;

cyclic ether solvents such as tetrahydrofuran and tetrahydropyran; and the like.

Examples of the ester solvent include:

acetic acid ester solvents such as methyl acetate, ethyl acetate, n-propyl acetate, iso-propyl acetate, n-butyl acetate, iso-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, glycol diacetate and methoxytriglycol acetate;

polyhydric alcohol partial ether acetate solvents such as ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate and dipropylene glycol monoethyl ether acetate;

carbonic acid ester solvents such as dimethyl carbonate and diethyl carbonate;

other carboxylic acid ester solvents such as methyl acetoacetate, ethyl acetoacetate, ethyl propionate, n-butyl propionate, iso-amyl propionate, diethyl oxalate, di-n-butyl oxalate, methyl lactate, ethyl lactate, n-butyl lactate, n-amyl lactate, diethyl malonate, dimethyl phthalate and diethyl phthalate; and the like.

Of these, a ketone solvent and an ester solvent are preferred. As the ketone solvent, a cyclic ketone solvent is more preferred, and cyclohexanone is still more preferred, and as the ester solvent, polyhydric alcohol partial ether acetate solvent is more preferred, and propylene glycol monomethyl ether acetate is still more preferred.

(G) Uneven Distribution Accelerator

The uneven distribution accelerator (G) is a component that more efficiently segregates the polymer (E) on the surface of the resist film. When the radiation-sensitive resin composition contains the uneven distribution accelerator (G), the polymer (E) can be segregated more effectively on the surface of the resist film, thereby enabling the amount of the polymer (E) to be decreased. The uneven distribution accelerator (G) is exemplified by a lactone compound, a carbonate compound, a nitrile compound, a polyhydric alcohol, and the like. The uneven distribution accelerator (G) may be used either alone of one type, or in combination of two or more types thereof.

Examples of the lactone compound include γ-butyrolactone, valerolactone, mevalonic lactone, norbornanelactone, and the like.

Examples of the carbonate compound include propylene carbonate, ethylene carbonate, butylene carbonate, vinylene carbonate, and the like.

Examples of the nitrile compound include succinonitrile, and the like.

Examples of the polyhydric alcohol include glycerin, and the like.

Of these, a lactone compound is preferred, and γ-butyrolactone is more preferred.

The content of the uneven distribution accelerator (G) is preferably 5 parts by mass to 300 parts by mass, more preferably 10 mass to 100 parts by mass, and still more preferably 20 parts by mass to 70 parts by mass with respect to 100 parts by mass of the polymer (A).

Other Optional Component

The radiation-sensitive resin composition may contain other optional component such as a surfactant, an alicyclic skeleton-containing compound and a sensitizing agent in addition to the aforementioned the components (A) to (G). The other optional components each may be used either alone or in combination of two or more types thereof. In addition, the content of the other optional components can be appropriately decided in accordance with the intended usage.

Surfactant

The surfactant exerts the effect of improving coating properties, striation, developability, and the like. Examples of the surfactant include: nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate; commercially available products such as KP341 (manufactured by Shin-Etsu Chemical Co., Ltd.), Polyflow No. 75 and Polyflow No. 95 (all manufactured by Kyoeisha Chemical Co., Ltd.), EFTOP EF301, EFTOP EF303 and EFTOP EF352 (all manufactured by Tochem Products Co. Ltd.), Megaface F171 and Megaface F173 (all manufactured by DIC), Fluorad FC430 and Fluorad FC431 (all manufactured by Sumitomo 3M Limited), and ASAHI GUARD AG710, Surflon S-382, Surflon SC-101, Surflon SC-102, Surflon SC-103, Surflon SC-104, Surflon SC-105 and Surflon SC-106 (all manufactured by Asahi Glass Co., Ltd.); and the like. The content of the surfactant in the radiation-sensitive resin composition is typically no greater than 2 parts by mass with respect to 100 parts by mass of the polymer (A).

Alicyclic Skeleton-Containing Compound

The alicyclic skeleton-containing compound exerts the effect of improving dry-etching resistance, a pattern configuration, adhesiveness to a substrate, and the like.

Examples of the alicyclic skeleton-containing compound include:

adamantane derivatives such as 1-adamantanecarboxylic acid, 2-adamantanone and t-butyl 1-adamantanecarboxylate;

deoxycholic acid esters such as t-butyl deoxycholate, t-butoxycarbonylmethyl deoxycholate and 2-ethoxyethyl deoxycholate;

lithocholic acid esters such as t-butyl lithocholate, t-butoxycarbonylmethyl lithocholate and 2-ethoxyethyl lithocholate;

3-[2-hydroxy-2,2-bis(trifluoromethyl)ethyl]tetracyclo[4.4.0.1$^{2,5}$.1$^{7,10}$]dodecane, and 2-hydroxy-9-methoxycarbonyl-5-oxo-4-oxa-tricyclo[4.2.1.0$^{3,7}$]nonane; and the like. The content of the alicyclic skeleton-containing compound in the radiation-sensitive resin composition is typically no greater than 5 parts by mass with respect to 100 parts by mass of the polymer (A).

Sensitizing Agent

The sensitizing agent exhibits the action of increasing the amount of the acid produced from the acid generating agent (C) or the like, and exerts the effect of improving "apparent sensitivity" of the radiation-sensitive resin composition.

Examples of the sensitizing agent include carbazoles, acetophenones, benzophenones, naphthalenes, phenols, biacetyl, eosin, rose bengal, pyrenes, anthracenes, phenothiazines, and the like. These sensitizing agents may be used either alone, or two or more types thereof may be used in combination. The content of the sensitizing agent in the radiation-sensitive resin composition is typically no greater than 2 parts by mass with respect to 100 parts by mass of the polymer (A).

Preparation Method of Radiation-Sensitive Resin Composition

The radiation-sensitive resin composition may be prepared, for example, by mixing the polymer (A), the compound (B) as well as each optional component such as the acid generator (C), the other acid diffusion controller (D), the polymer (E) and the solvent (F) as needed in a certain ratio. The solid content concentration of the radiation-sensitive resin composition is preferably 0.1% by mass to 50% by mass, more preferably 0.5% by mass to 30% by mass, and still more preferably 1% by mass to 10% by mass.

Resist Pattern-Forming Method

A resist pattern-forming method according to another embodiment of the present invention includes:

providing a resist film using the radiation-sensitive resin composition according to the embodiment of the present invention (hereinafter, may be also referred to as "resist film-providing step");

exposing the resist film (hereinafter, may be also referred to as "exposure step"); and developing the exposed resist film (hereinafter, may be also referred to as "development step"). Hereinafter, each step will be explained.

Resist Film-Providing Step

In this step, a resist film is provided using the aforementioned radiation-sensitive resin composition according to the embodiment of the present invention. An application procedure is not particularly limited, and an appropriate application means such as spin-coating, cast coating and roll coating may be employed, for example. A substrate is exemplified by a silicon wafer, a wafer coated with aluminum, and the like. Specifically, the composition is applied such that the resulting resist film has a predetermined thickness, and thereafter prebaking (PB) is executed as needed to evaporate the solvent in the coating film. The film thickness of the coating film is preferably 10 nm to 500 nm. The temperature of the PB is typically 60° C. to 140° C., and preferably 80° C. to 120° C. The time period of the PB is typically 5 sec to 600 sec, and preferably 10 sec to 300 sec.

Exposure Step

In this step, the resist film provided in the resist film-providing step is exposed. The exposure may be executed by irradiating the resist film with a radioactive ray through a mask having a given pattern, and through a liquid immersion medium such as water, as needed. The radioactive ray may be appropriately selected from electromagnetic waves such as a visible light ray, an ultraviolet ray, a far ultraviolet ray, an EUV (wavelength: 13.5 nm), an X-ray and a γ-radiation; charged particle rays such as an electron beam and an α-ray; and the like in accordance with the line width of the intended pattern. Of these, in a case where the polymer (A) of the radiation-sensitive resin composition has the structural unit (I-1), or the like, far ultraviolet rays are preferred, an ArF excimer laser beam (wavelength: 193 nm) and a KrF excimer laser beam (wavelength: 248 nm) are more preferred, and an ArF excimer laser beam is still more preferred. Alternatively, in a case where the polymer (A) of the radiation-sensitive resin composition has the structural unit (I-2), or the like, an electron beam and an EUV are preferred.

Moreover, post exposure baking (PEB) is preferably carried out after the exposure. The PEB allows the dissociation reaction of the acid-labile group to proceed smoothly at an exposed site of the resist film. The temperature of the PEB is typically 50° C. to 180° C., and preferably 80° C. to 130° C. The time period of the PEB is typically 5 sec to 600 sec, and preferably 10 sec to 300 sec.

In the embodiment of the present invention, in order to maximize the potential capability of the radiation-sensitive resin composition, an organic or inorganic antireflective film, for example, may be also formed on the substrate employed. Moreover, in order to prevent influences of basic impurities etc., included in the environment atmosphere, a protective film, for example, may be also provided on the coating film. In addition, in a case where the exposure is executed through a liquid immersion medium, in order to avoid a direct contact of the liquid immersion medium with the resist film, a protective film for liquid immersion, for example, may be provided on the resist film.
Development Step In this step, the resist film exposed in the exposure step is developed. A developer solution for use in this development is exemplified by an alkaline developer solution, an organic solvent developer solution, and the like. Thus, a predetermined resist pattern can be formed.

Examples of the alkaline developer solution include aqueous alkaline solutions prepared by dissolving at least one alkaline compound such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide (TMAH), pyrrole, piperidine, choline, 1,8-diazabicyclo-[5.4.0]-7-undecene, and 1,5-diazabicyclo-[4.3.0]-5-nonene; and the like.

Examples of the organic solvent developer solution include:

alcohol solvents such as methanol, ethanol, n-propanol, iso-propanol, n-butanol, iso-butanol and sec-butanol;

ether solvents such as diethyl ether, dipropyl ether, dibutyl ether, tetrahydrofuran, dioxane, diphenyl ether and anisole;

ketone solvents such as acetone, methyl ethyl ketone, methyl n-propyl ketone and methyl n-butyl ketone;

amide solvents such as N,N'-dimethylimidazolidinone, N-methylformamide and N,N-dimethylformamide;

ester solvents such as diethyl carbonate, methyl acetate, ethyl acetate, n-propyl acetate, iso-propyl acetate and n-butyl acetate.

These developer solutions may be used either alone or in combination of two or more types thereof. It is to be noted that after the development, washing with water or the like and drying are typically carried out.
Radiation-Sensitive Acid Generating Agent A radiation-sensitive acid generating agent according to still another embodiment of the present invention contains the compound represented by the above formula (1). Since the radiation-sensitive acid generating agent exhibits the aforementioned characteristics, the radiation-sensitive acid generating agent can improve the LWR performance and the like of the radiation-sensitive resin composition.
Compound A compound according to yet still another embodiment of the present invention is represented by the above formula (1). Since the compound has the aforementioned structure, the compound can be suitably used as a compound constituting the radiation-sensitive acid generating agent.
Production Method of Compound A method for producing a compound represented by the following formula (1) according to even yet still another embodiment of the present invention includes:

(A) reacting an organic halide represented by the following formula (i-a) with a sulfurous acid salt represented by $E_2SO_3$ to obtain an organic sulfurous acid salt represented by the following formula (i-b); and (B) reacting the organic sulfurous acid salt with an onium salt represented by MY.

According to the method for producing the compound, the compound can be produced conveniently in a favorable yield.

The radiation-sensitive acid generating agent, the compound and the method for producing the compound have been described in the section "(B) Compound" in connection with the aforementioned radiation-sensitive resin composition.

EXAMPLES

Hereinafter, the present invention is explained in detail by way of Examples, but the present invention is not in any way limited to these Examples. Measuring methods for various types of physical properties are shown below.

Weight Average Molecular Weight (Mw) and Number Average Molecular Weight (Mn)

The Mw and the Mn were determined by gel permeation chromatography (GPC) using GPC columns (G2000 HXL×2, G3000 HXL×1, and G4000 HXL×1) manufactured by Tosoh Corporation, a differential refractometer as a detector, and mono-dispersed polystyrene as a standard under analytical conditions involving a flow rate of 1.0 mL/min, an elution solvent of tetrahydrofuran, a sample concentration of 1.0% by mass, an amount of injected sample of 100 µL, and a column temperature of 40° C. The dispersity index (Mw/Mn) was calculated based on the results of the determination of the Mw and the Mn.

$^{13}$C-NMR Analysis

A $^{13}$C-NMR analysis for the determination of the proportions of each structural unit contained in each polymer was carried out using JNM-ECX400 manufactured by JEOL, Ltd., and deuterochloroform as a solvent for measurement.

Production of Compound

Example 1

Synthesis of Compound (S-1)

A compound represented by the following formula (S-1) was produced in accordance with the following scheme.

Into a 1,000 mL eggplant-shaped flask were charged 10.0 g (111 mmol) of oxalic acid, 6.78 g (55.5 mmol) of dimethylaminopyridine (DMAP, a compound represented by the following formula (a-1)), 10.6 g (55.5 mmol) of 1-ethyl-3-[3-(dimethylamino)propyl]carbodiimide hydrochloride (EDCI) (a compound represented by the following formula (a-2)) and 300 mL of dichloromethane as a solvent, and stirred. To this, 150 mL of a solution of 8.45 g (55.5 mmol) of 1-adamantanol in dichloromethane was slowly added dropwise at room temperature. After stirring at room temperature for 48 hrs, the reaction was stopped through addition of dilute hydrochloric acid. Next, the dichloromethane phase was collected, concentrated, and thereafter purified by column chromatography to obtain 7.22 g (yield: 58%) of a monosubstituted oxalic acid ester product.

Subsequently, 2.00 g (8.92 mmol) of the monosubstituted oxalic acid ester product was dissolved in 15 g of tetrahydrofuran, and 10 g of water was further added. To this, 0.357 g (8.92 mmol) of sodium hydroxide was added in solid state, and the mixture was stirred at room temperature for 1 hour. Next, after the solvent was distilled off, 2.67 g (8.92 mmol) of triphenylsulfonium chloride, 60 mL of dichloromethane and 60 mL of water were added, and the mixture was stirred at room temperature for 6 hrs. Then, the organic phase was recovered, and washed five times with water. Then, after the solvent was distilled off, purification by column chromatography was carried out to obtain 3.26 g (yield: 75%) of a compound (S-1).

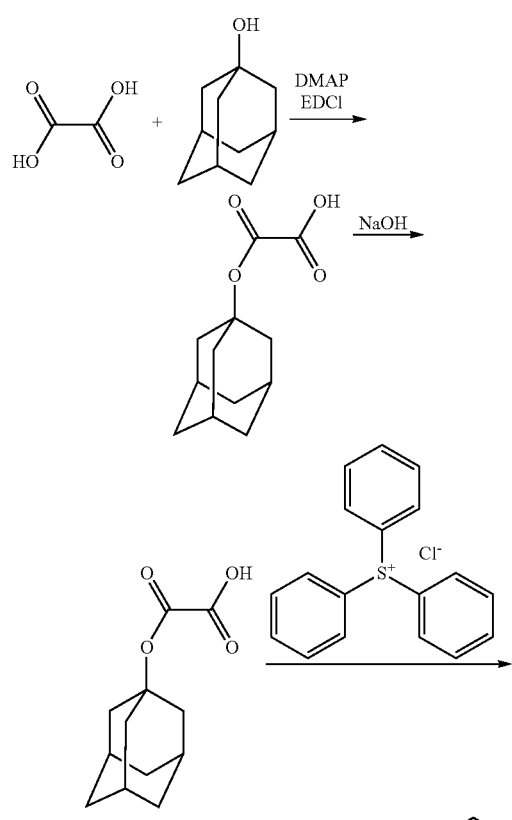
(S-1)
(a-1)
(a-2)
Examples 2 to 16
Production of Compounds (S-2) to (S-16)
Compounds represented by the following formulae (S-2) to (S-16) were synthesized by a similar operation to Example 1, through appropriately selecting a precursor.
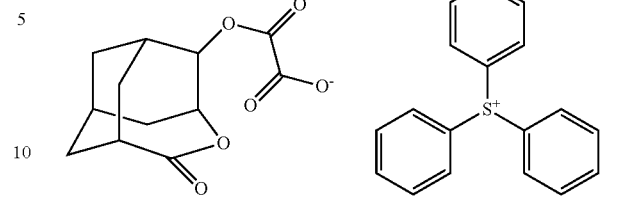
(S-2)
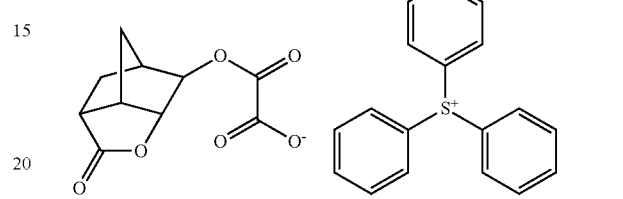
(S-3)
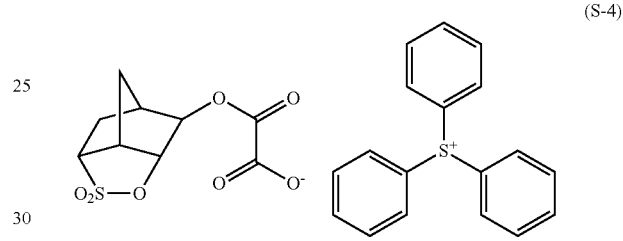
(S-4)
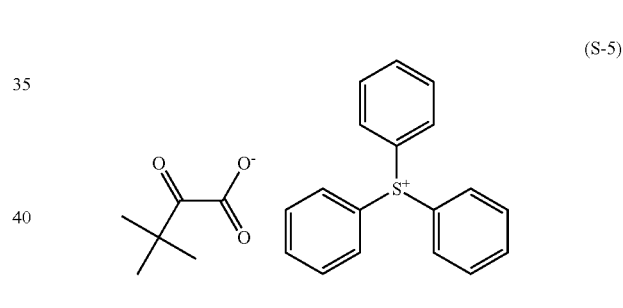
(S-5)
(S-6)
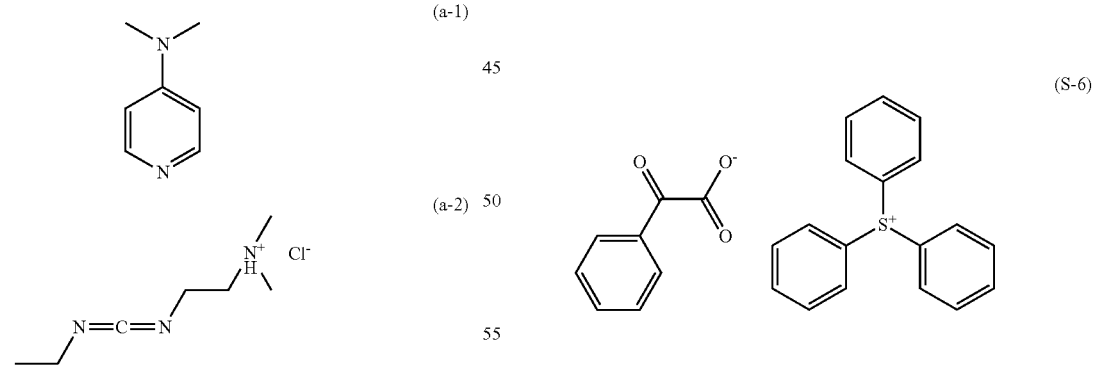
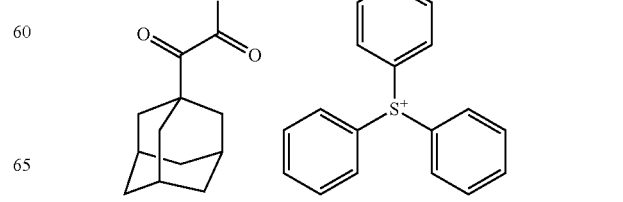
(S-7)

(S-8) 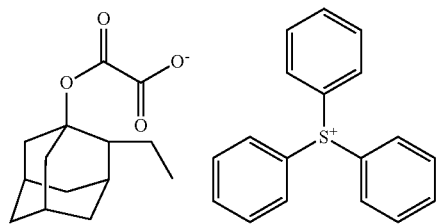
(S-9) 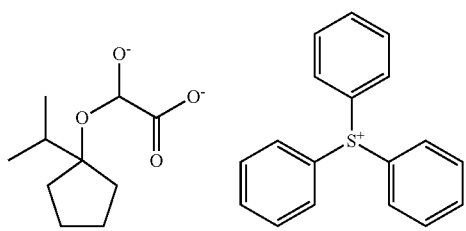
(S-10) 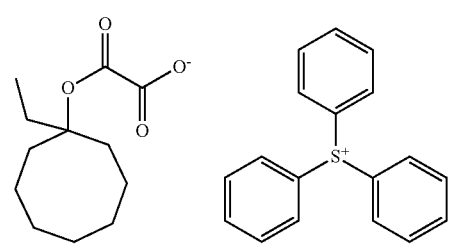
(S-11) 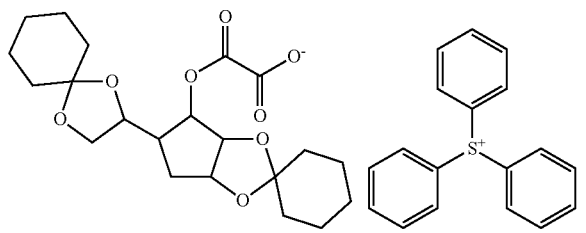
(S-12) 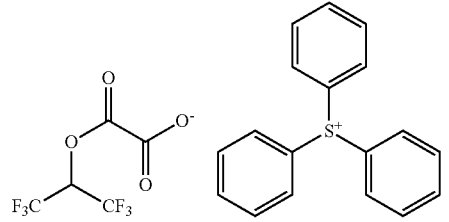
(S-13) 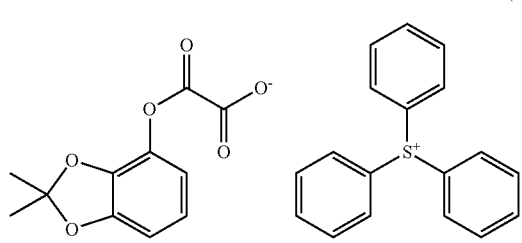
(S-14) 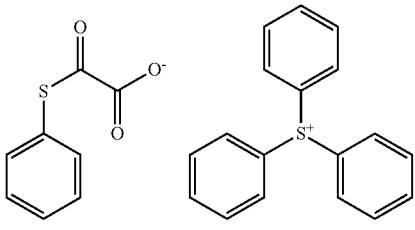
(S-15) 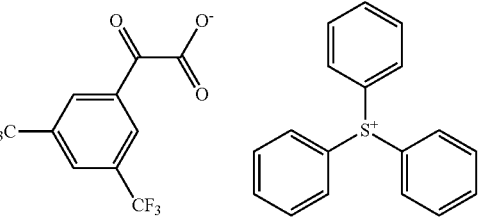
(S-16) 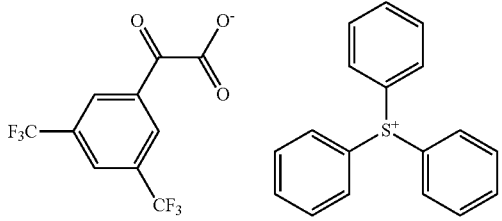
Production of Polymer (A) and Polymer (E)
Monomers which were used in the production of each polymer are shown below.
(M-1) 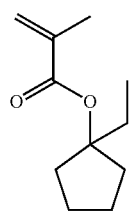
(M-2) 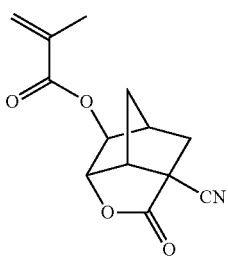
(M-3) 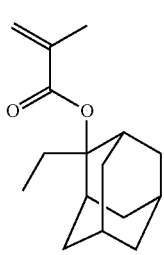

-continued (M-4) 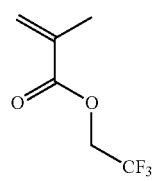

(M-5) 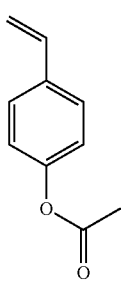

(M-6) 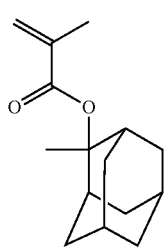

(M-7) 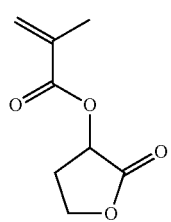

(M-8) 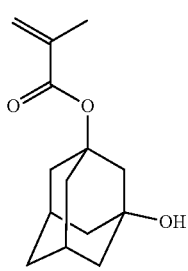

(M-9) 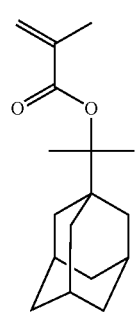

-continued (M-10) 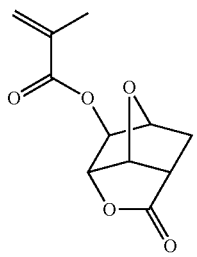

(M-11) 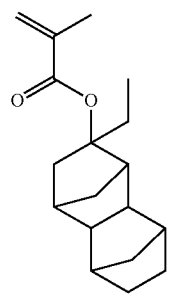

Production of Polymer (A)

Synthesis Example 1

Production of Polymer (A-1)

A monomer solution was prepared by dissolving 7.97 g (35 mol %) of the compound (M-6), 7.44 g (45 mol %) of the compound (M-7) and 4.49 g (20 mol %) of the compound (M-8) in 40 g of 2-butanone, and further adding thereto 0.80 g (5 mol % with respect to the total number of moles of the compounds) of AIBN as a radical initiator. A 100 mL three-neck flask containing 20 g of 2-butanone was purged with nitrogen for 30 min, then heated to 80° C. with stirring, and the monomer solution prepared above was added dropwise over 3 hrs using a dropping funnel. The time of the start of the dropwise addition was regarded as the time of the start of the polymerization reaction, and the polymerization reaction was allowed to proceed for 6 hrs. After the completion of the polymerization reaction, the polymerization reaction solution was water-cooled to 30° C. or below. The cooled polymerization reaction solution was poured into 400 g of methanol, and a precipitated white powder was filtered off. The collected white powder was washed twice with 80 g of methanol, followed by filtration, and dried at 50° C. for 17 hrs, whereby a polymer (A-1) was obtained as a white powder (15.2 g; yield: 76%). The polymer (A-1) had an Mw of 7,300 and an Mw/Mn of 1.53. The result of the $^{13}$C-NMR analysis indicated that the proportions of the structural unit derived from (M-6), the structural unit derived from (M-7) and the structural unit derived from (M-8) were 34.3 mol %, 45.1 mol % and 20.6 mol %, respectively.

Synthesis Example 2

Production of Polymer (A-2)

A monomer solution was prepared by dissolving 6.88 g (40 mol %) of the compound (M-1), 2.30 g (10 mol %) of the compound (M-9) and 10.83 g (50 mol %) of the compound (M-2) in 40 g of 2-butanone, and adding thereto 0.72 g (5 mol % with respect to the total number of moles of the compounds) of AIBN as a radical initiator. A 100 mL three-neck flask containing 20 g of 2-butanone was purged with nitrogen for 30 min, then heated to 80° C. with stirring, and the monomer solution prepared above was added dropwise over 3 hrs using a dropping funnel. The time of the start of the dropwise addition was regarded as the time of the start of the polymerization reaction, and the polymerization reaction was allowed to proceed for 6 hrs. The resulting polymerization reaction solution was treated in a similar manner to Synthesis Example 1 described above, whereby a polymer (A-2) (14.9 g; yield: 75%) was obtained as a white powder. The polymer (A-2) had an Mw of 7,500 and an Mw/Mn of 1.55. The result of the $^{13}$C-NMR analysis indicated that the proportions of the structural unit derived from (M-1), the structural unit derived from (M-9) and the structural unit derived from (M-2) were 40.1 mol %, 10.1 mol % and 49.8 mol %, respectively.

Synthesis Example 3

Production of Polymer (A-3)

A monomer solution was prepared by dissolving 3.43 g (20 mol %) of the compound (M-1), 3.59 g (15 mol %) of the compound (M-11), 7.83 g (40 mol %) of the compound (M-10) and 5.16 g (25 mol %) of the compound (M-8) in 40 g of 2-butanone, and adding thereto 0.72 g (5 mol % with respect to the total number of moles of the compounds) of AIBN as a radical initiator. A 100 mL three-neck flask containing 20 g of 2-butanone was purged with nitrogen for 30 min, then heated to 80° C. with stirring, and the monomer solution prepared above was added dropwise over 3 hrs using a dropping funnel. The time of the start of the dropwise addition was regarded as the time of the start of the polymerization reaction, and the polymerization reaction was allowed to proceed for 6 hrs. The resulting polymerization reaction solution was treated in a similar manner to Synthesis Example 1 described above, whereby a polymer (A-3) (15.3 g; yield: 77%) was obtained as a white powder. The polymer (A-3) had an Mw of 7,200 and an Mw/Mn of 1.53. The result of the $^{13}$C-NMR analysis indicated that the proportions of the structural unit derived from (M-1), the structural unit derived from (M-11), the structural unit derived from (M-10) and the structural unit derived from (M-8) were 19.5 mol %, 15.5 mol %, 40.1 mol % and 24.9 mol %, respectively.

Synthesis Example 4

Synthesis of Polymer (A-4)

After 55.0 g (65 mol %) of the compound (M-5), 45.0 g (35 mol %) of the compound (M-3), 4 g of AIBN as a radical initiator and 1 g of t-dodecyl mercaptan as a chain transfer agent were dissolved in 100 g of propylene glycol monomethyl ether, the mixture was subjected to polymerization for 16 hrs under a nitrogen atmosphere, while the reaction temperature was maintained at 70° C. After the completion of the polymerization reaction, the polymerization reaction solution was added dropwise to 1,000 g of n-hexane to permit solidification purification of a polymer. Next, to the obtained polymer was added 150 g of propylene glycol monomethyl ether again, and then 150 g of methanol, 34 g of triethylamine and 6 g of water were added. The mixture was subjected to a hydrolysis reaction for 8 hrs while refluxing at the boiling point. After the completion of the reaction, the solvent and triethylamine were distilled off in vacuo. The obtained polymer was dissolved in 150 g of acetone, then the solution was added dropwise to 2,000 g of water to permit solidification, and the obtained white powder was filtered off and dried at 50° C. for 17 hrs to obtain a polymer (A-4) as a white powder (65.7 g; yield: 77%). The polymer (A-4) had an Mw of 7,500 and an Mw/Mn of 1.90. The result of the $^{13}$C-NMR analysis indicated that the proportions of the structural unit derived from p-hydroxystyrene and the structural unit derived from (M-3) were 65.4 mol % and 34.6 mol %, respectively.

Production of Polymer (E)

Synthesis Example 5

Synthesis of Polymer (E-1)

A monomer solution was prepared by dissolving 79.9 g (70 mol %) of the compound (M-1) and 20.91 g (30 mol %) of the compound (M-4) in 100 g of 2-butanone, and dissolving therein 4.77 g of dimethyl 2,2'-azobisisobutyrate as a radical initiator. A 1,000 mL three-neck flask containing 100 g of 2-butanone was purged with nitrogen for 30 min, then heated to 80° C. with stirring, and the monomer solution prepared above was added dropwise over 3 hrs using a dropping funnel. The time of the start of the dropwise addition was regarded as the time of the start of the polymerization reaction, and the polymerization reaction was allowed to proceed for 6 hrs. After the completion of the polymerization reaction, the polymerization reaction solution was water-cooled to 30° C. or below. After this polymerization reaction solution was transferred to a 2 L separatory funnel, the polymerization reaction solution was homogeneously diluted with 150 g of n-hexane. After the addition of 600 g of methanol, the components were mixed. Then, 30 g of distilled water was charged thereto, and the mixture was further stirred and then left to stand for 30 min. Thereafter, the lower layer was recovered and then the solvent was substituted to obtain a propylene glycol monomethyl ether acetate solution containing a polymer (E-1) (yield: 60%). The polymer (E-1) had an Mw of 7,200 and an Mw/Mn of 2.00. The result of the $^{13}$C-NMR analysis indicated that the proportions of the structural unit derived from (M-1) and the structural unit derived from (M-4) were 71.1 mol % and 28.9 mol %, respectively.

Preparation of Radiation-Sensitive Resin Compositions

The compound (B), the acid generating agent (C), the other acid diffusion control agent (D), the solvent (F) and the uneven distribution accelerator (G) which were used in the preparation of the radiation-sensitive resin compositions are shown below.

(B) Compound

The compounds (S-1) to (S-16) produced in Examples 1 to 16

(C) Acid Generating Agent

C-1: triphenylsulfonium 2-(adamantan-1-ylcarbonyloxy)-1,1,3,3,3-pentafluoropropane-1-sulfonate (a compound represented by the following formula (C-1))

C-2: triphenylsulfonium norbornanesulton-2-yloxycarbonyl-difluoromethanesulfonate (a compound represented by the following formula (C-2))

C-3: triphenylsulfonium 3-(piperidin-1-ylsulfonyl)-1,1,2,2,3,3-hexafluoropropane-1-sulfonate (a compound represented by the following formula (C-3))

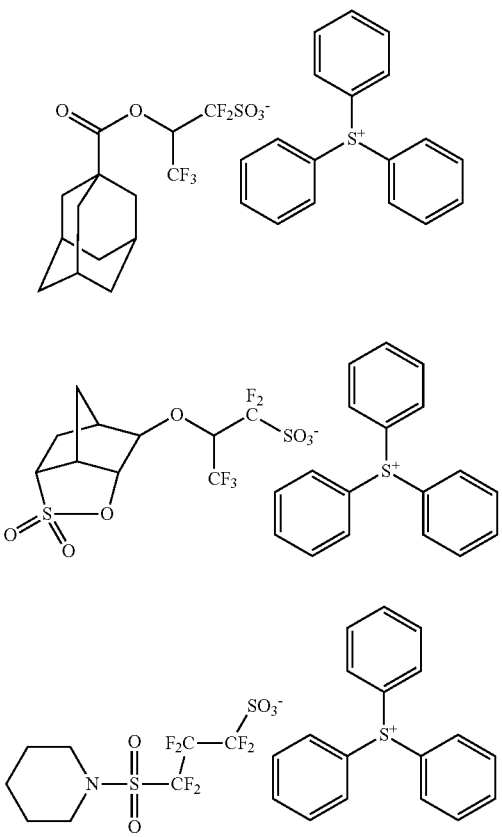

(C-1)

(C-2)

(C-3)

(D) Other Acid Diffusion Control Agent
D-1: triphenylsulfonium salicylate (a compound represented by the following formula (D-1))
D-2: triphenylsulfonium 10-camphorsulfonate (a compound represented by the following formula (D-2))
D-3: N-undecylcarbonyloxyethylmorpholine (a compound represented by the following formula (D-3))
D-4: 2,6-diisopropylaniline (a compound represented by the following formula (D-4))
D-5: tri-n-pentylamine (a compound represented by the following formula (D-5))

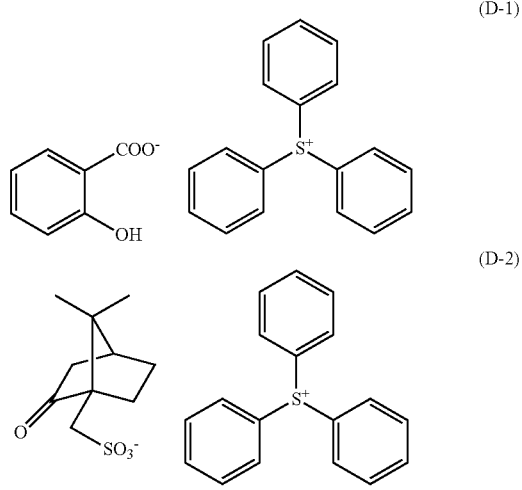

(D-1)

(D-2)

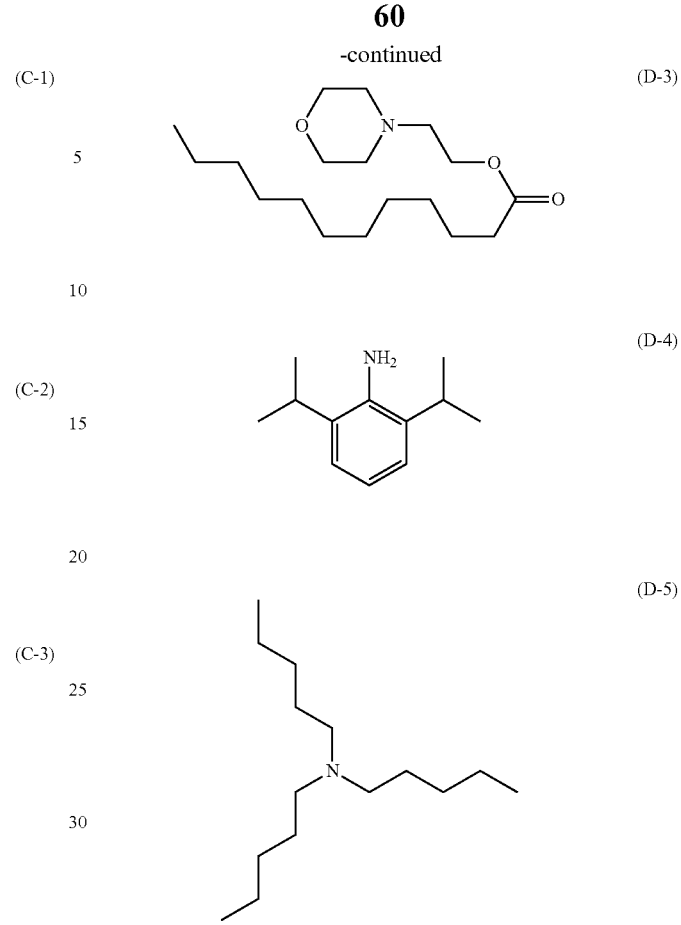

(D-3)

(D-4)

(D-5)

(F) Solvent
F-1: propylene glycol monomethyl ether acetate
F-2: cyclohexanone
(G) Uneven Distribution Accelerator
G-1: γ-butyrolactone Preparation of Radiation-Sensitive Resin Composition (I)

Example 17

A radiation-sensitive resin composition (J-1) was prepared by mixing 100 parts by mass of (A-1) as the polymer (A), 2.3 parts by mass of (S-1) as the compound (B), 8.5 parts by mass of (C-1) as the acid generating agent (C), 3 parts by mass of (E-1) as the polymer (E), 2,240 parts by mass of (F-1) and 960 parts by mass of (F-2) as the solvent (F), and 30 parts by mass of (G-1) as the uneven distribution accelerator (G).

Examples 18 to 38 and Comparative Examples 1 to 5

Radiation-sensitive resin compositions (J-2) to (J-22) and (CJ-1) to (CJ-5) were prepared in a similar manner to Example 1 except that the type and the content of each component used were as specified in Tables 1-1 and 1-2.

TABLE 1-1

| Radiation-sensitive resin composition | (A) Polymer type | (A) Polymer content (parts by mass) | (B) Compound/(D) Other acid diffusion control agent type | (B) Compound/(D) Other acid diffusion control agent content (parts by mass) | (C) Acid generating agent type | (C) Acid generating agent content (parts by mass) | (E) Polymer type | (E) Polymer content (parts by mass) | (F) Solvent type | (F) Solvent content (parts by mass) | (G) Uneven distribution accelerator type | (G) Uneven distribution accelerator content (parts by mass) |
|---|---|---|---|---|---|---|---|---|---|---|---|---|
| Example 17 | J-1 | A-1 | 100 | S-1 | 2.3 | C-1 | 8.5 | E-1 | 3 | F-1/F-2 | 2,240/960 | G-1 | 30 |
| Example 18 | J-2 | A-1 | 100 | S-2 | 2.3 | C-1 | 8.5 | E-1 | 3 | F-1/F-2 | 2,240/960 | G-1 | 30 |
| Example 19 | J-3 | A-1 | 100 | S-3 | 2.3 | C-1 | 8.5 | E-1 | 3 | F-1/F-2 | 2,240/960 | G-1 | 30 |
| Example 20 | J-4 | A-1 | 100 | S-4 | 2.3 | C-1 | 8.5 | E-1 | 3 | F-1/F-2 | 2,240/960 | G-1 | 30 |
| Example 21 | J-5 | A-1 | 100 | S-5 | 2.3 | C-1 | 8.5 | E-1 | 3 | F-1/F-2 | 2,240/960 | G-1 | 30 |
| Example 22 | J-6 | A-1 | 100 | S-6 | 2.3 | C-1 | 8.5 | E-1 | 3 | F-1/F-2 | 2,240/960 | G-1 | 30 |
| Example 23 | J-7 | A-1 | 100 | S-7 | 2.3 | C-1 | 8.5 | E-1 | 3 | F-1/F-2 | 2,240/960 | G-1 | 30 |
| Example 24 | J-8 | A-2 | 100 | S-1 | 2.3 | C-2 | 8.5 | E-1 | 3 | F-1/F-2 | 2,240/960 | G-1 | 30 |
| Example 25 | J-9 | A-3 | 100 | S-1 | 2.3 | C-2 | 8.5 | E-1 | 3 | F-1/F-2 | 2,240/960 | G-1 | 30 |
| Example 26 | J-10 | A-2 | 100 | S-1 | 2.3 | C-3 | 8.5 | E-1 | 3 | F-1/F-2 | 2,240/960 | G-1 | 30 |
| Example 27 | J-11 | A-3 | 100 | S-1 | 2.3 | C-3 | 8.5 | E-1 | 3 | F-1/F-2 | 2,240/960 | G-1 | 30 |
| Example 28 | J-12 | A-1 | 100 | S-8 | 2.3 | C-1 | 8.5 | E-1 | 3 | F-1/F-2 | 2,240/960 | G-1 | 30 |
| Example 29 | J-13 | A-1 | 100 | S-9 | 2.3 | C-1 | 8.5 | E-1 | 3 | F-1/F-2 | 2,240/960 | G-1 | 30 |
| Example 30 | J-14 | A-1 | 100 | S-10 | 2.3 | C-1 | 8.5 | E-1 | 3 | F-1/F-2 | 2,240/960 | G-1 | 30 |

TABLE 1-2

| Radiation-sensitive resin composition | (A) Polymer type | (A) Polymer content (parts by mass) | (B) Compound/(D) Other acid diffusion control agent type | (B) Compound/(D) Other acid diffusion control agent content (parts by mass) | (C) Acid generating agent type | (C) Acid generating agent content (parts by mass) | (E) Polymer type | (E) Polymer content (parts by mass) | (F) Solvent type | (F) Solvent content (parts by mass) | (G) Uneven distribution accelerator type | (G) Uneven distribution accelerator content (parts by mass) |
|---|---|---|---|---|---|---|---|---|---|---|---|---|
| Example 31 | J-15 | A-1 | 100 | S-11 | 2.3 | C-1 | 8.5 | E-1 | 3 | F-1/F-2 | 2,240/960 | G-1 | 30 |
| Example 32 | J-16 | A-1 | 100 | S-12 | 2.3 | C-1 | 8.5 | E-1 | 3 | F-1/F-2 | 2,240/960 | G-1 | 30 |
| Example 33 | J-17 | A-1 | 100 | S-13 | 2.3 | C-1 | 8.5 | E-1 | 3 | F-1/F-2 | 2,240/960 | G-1 | 30 |
| Example 34 | J-18 | A-1 | 100 | S-14 | 2.3 | C-1 | 8.5 | E-1 | 3 | F-1/F-2 | 2,240/960 | G-1 | 30 |
| Example 35 | J-19 | A-1 | 100 | S-15 | 2.3 | C-1 | 8.5 | E-1 | 3 | F-1/F-2 | 2,240/960 | G-1 | 30 |
| Example 36 | J-20 | A-1 | 100 | S-16 | 2.3 | C-1 | 8.5 | E-1 | 3 | F-1/F-2 | 2,240/960 | G-1 | 30 |
| Example 37 | J-21 | A-1 | 100 | S-1 / S-9 | 1.1 / 1.2 | C-1 | 8.5 | E-1 | 3 | F-1/F-2 | 2,240/960 | G-1 | 30 |
| Example 38 | J-22 | A-1 | 100 | S-1 / D-3 | 1.1 / 1.2 | C-1 | 8.5 | E-1 | 3 | F-1/F-2 | 2,240/960 | G-1 | 30 |
| Comparative Example 1 | CJ-1 | A-1 | 100 | D-1 | 2.3 | C-1 | 8.5 | E-1 | 3 | F-1/F-2 | 2,240/960 | G-1 | 30 |
| Comparative Example 2 | CJ-2 | A-2 | 100 | D-2 | 2.3 | C-2 | 8.5 | E-1 | 3 | F-1/F-2 | 2,240/960 | G-1 | 30 |
| Comparative Example 3 | CJ-3 | A-3 | 100 | D-3 | 2.3 | C-3 | 8.5 | E-1 | 3 | F-1/F-2 | 2,240/960 | G-1 | 30 |
| Comparative Example 4 | CJ-4 | A-2 | 100 | D-4 | 2.3 | C-2 | 8.5 | E-1 | 3 | F-1/F-2 | 2,240/960 | G-1 | 30 |
| Comparative Example 5 | CJ-5 | A-3 | 100 | D-5 | 2.3 | C-3 | 8.5 | E-1 | 3 | F-1/F-2 | 2,240/960 | G-1 | 30 |

Formation of Resist Pattern (1)

An underlayer antireflective film having a film thickness of 105 nm was provided on the surface of a 12-inch silicon wafer by applying a composition for underlayer antireflective film formation (ARC66, manufactured by Brewer Science) on the surface of the 12-inch silicon wafer using a spin coater (CLEAN TRACK ACT12, manufactured by Tokyo Electron Limited), and thereafter heating the same at 205° C. for 60 sec. Each radiation-sensitive resin composition prepared above was applied on the underlayer antireflective film using the spin coater, and subjected to PB at 90° C. for 60 sec. Thereafter, cooling was carried out at 23° C. for 30 sec to provide a resist film having a film thickness of 90 nm. Next, the resist film was exposed using an ArF excimer laser Immersion Scanner (NSR-S610C, manufactured by NIKON) through a 40 nm line-and-space (1L1S) mask pattern, under optical conditions involving NA of 1.3 and dipole (Sigma: 0.977/0.782). After the exposure, PEB was carried out at 90° C. for 60 sec. Thereafter, a development was carried out with a 2.38% by mass aqueous TMAH solution as an alkaline developer solution, followed by washing with water and drying to form a positive type resist pattern. In this resist pattern formation, an exposure dose at which a 1:1 line-and-space with a line width of 40 nm was formed through a mask for the 1:1 line-and-space with a target dimension of 40 nm was defined as an "optimum exposure dose (Eop (1))".

Formation of Resist Pattern (2)

A negative type resist pattern was formed in the same manner to that of the above Formation of Resist Pattern (1) except that: n-butyl acetate as an organic solvent developer solution was used in place of the aqueous TMAH solution to execute a development with an organic solvent; and washing with water was not carried out. In this resist pattern formation, an exposure dose at which a 1:1 line-and-space with a line width of 40 nm was formed through a mask for the 1:1 line-and-space with a target dimension of 40 nm was defined as an "optimum exposure dose (Eop (2))".

Evaluations

Measurements were made on the resist patterns obtained in Formation of Resist Pattern (1) and Formation of Resist Pattern (2) described above in accordance with the following methods to evaluate the radiation-sensitive resin compositions in regard to the LWR performance, the resolution, the rectangularity of the cross-sectional shape, and the depth of focus. The results of the evaluations are shown in Table 2. For a line-width measurement of the resist patterns, a scanning electron microscope (S-9380, manufactured by Hitachi High-Technologies Corporation) was used. It is to be noted that comparisons were made with, as a standard: Comparative Example 1 for Examples 17 to 23 and 28 to 38; Comparative Example 2 for Example 24; Comparative Example 3 for Example 25; Comparative Example 4 for Example 26; Comparative Example 5 for Example 27, whereby evaluations were made. In Table 2, "—" denotes being a decision standard.

LWR Performance

The obtained resist pattern was observed from above the pattern, and the line width was measured at arbitrary points of 50 in total, and a 3 Sigma value was determined from the distribution of the measurements, and the value was defined as "LWR performance". The smaller value indicates a better LWR performance. By comparing the "LWR performance" value with that for the Comparative Example to be compared (decision standard), the evaluation of the "LWR performance" was made as: "A" when an improvement of the "LWR performance" of no less than 10% (i.e., the "LWR performance" value accounting for no greater than 90% of the value for the standard Comparative Example) was found; "B" when an improvement of the "LWR performance" of less than 10% (i.e., the "LWR performance" value accounting for greater than 90% and no greater than 100%) was found; and "C" when the "LWR performance" was comparable or deteriorated (i.e., the value of the "LWR performance" value accounting for no less than 100%).

Resolution

A dimension of the minimum resist pattern which was resolved at the optimum exposure dose (Eop (1) or Eop (2)) was measured, and the dimension was defined as "resolution". The smaller measurement indicates a better resolution. By comparing the "resolution" value with that for the Comparative Example to be compared (decision standard), the evaluation of the resolution was made as: "A" when an improvement of the "resolution" of no less than 10% (i.e., the "resolution" value accounting for no greater than 90% of the value for the standard Comparative Example) was found; "B" when an improvement of the "resolution" of less than 10% (i.e., the "resolution" value accounting for greater than 90% and no greater than 100%) was found; and "C" when the "resolution" was comparable or deteriorated (i.e., the "resolution" value accounting for no less than 100%).

Rectangularity of Cross-Sectional Shape

A cross-sectional shape of the resist pattern which was resolved at the optimum exposure dose (Eop (1) or Eop (2)) was observed to measure a line width Lb in the middle along an altitude direction of the resist pattern, and a line width La on the top of the film. The rectangularity of the cross-sectional shape was evaluated as: "A" in a case where $0.9 \leq (La/Lb) \leq 1.1$; and as "B" in a case where $(La/Lb) < 0.9$, or $1.1 < (La/Lb)$.

Depth of Focus

On the resist pattern which was resolved at the optimum exposure dose (Eop (1) or Eop (2)), the dimension of a pattern formed when the focus was shifted along the depth direction was observed, a latitude in the depth direction in which the pattern dimension falls within the range of 90% to 110% of the standard without being accompanied by a bridge and/or residue was determined, and the measurement value was defined as "depth of focus". The greater depth of focus indicates a more favorable result. By comparing the "depth of focus" value with that for the Comparative Example to be compared (decision standard), the evaluation of the depth of focus was made as: "A" when an improvement of the "depth of focus" of no less than 10% (i.e., the "depth of focus" value accounting for no less than 110% of the value for the standard Comparative Example) was found; "B" when an improvement of the "depth of focus" of less than 10% (i.e., the "depth of focus" value accounting for greater than 100% and no greater than 110%) was found; and "C" when the "depth of focus" was comparable or deteriorated (i.e., the "depth of focus" value accounting for no greater than 100%).

TABLE 2

| | Radiation-sensitive resin composition | Development with alkali | | | | Development with organic solvent | | | |
|---|---|---|---|---|---|---|---|---|---|
| | | LWR performance | resolution | rectangularity of cross-sectional shape | depth of focus | LWR performance | resolution | rectangularity of cross-sectional shape | depth of focus |
| Example 17 | J-1 | A | A | A | A | A | A | A | A |
| Example 18 | J-2 | A | B | A | B | A | B | B | A |
| Example 19 | J-3 | A | B | B | B | A | A | B | B |
| Example 20 | J-4 | A | B | A | A | B | A | A | B |
| Example 21 | J-5 | B | B | B | B | B | B | B | B |
| Example 22 | J-6 | A | A | A | B | A | A | B | A |
| Example 23 | J-7 | A | B | B | A | A | A | B | B |
| Example 24 | J-8 | A | A | B | A | A | A | A | A |
| Example 25 | J-9 | A | A | A | A | A | A | A | A |
| Example 26 | J-10 | A | A | A | A | B | A | A | A |
| Example 27 | J-11 | A | A | A | A | A | A | A | B |
| Example 28 | J-12 | A | A | A | A | A | A | A | A |
| Example 29 | J-13 | A | A | A | A | A | A | A | A |
| Example 30 | J-14 | A | A | A | A | A | A | A | A |
| Example 31 | J-15 | A | A | A | A | A | A | A | A |
| Example 32 | J-16 | B | B | B | B | B | B | B | B |
| Example 33 | J-17 | B | B | B | B | B | B | B | B |
| Example 34 | J-18 | B | B | B | B | B | B | B | B |

TABLE 2-continued

|  | Radiation-sensitive resin composition | Development with alkali | | | | Development with organic solvent | | | |
|---|---|---|---|---|---|---|---|---|---|
|  |  | LWR performance | resolution | rectangularity of cross-sectional shape | depth of focus | LWR performance | resolution | rectangularity of cross-sectional shape | depth of focus |
| Example 35 | J-19 | A | A | A | A | A | A | A | A |
| Example 36 | J-20 | B | B | B | B | B | B | B | B |
| Example 37 | J-21 | A | A | A | A | A | A | A | A |
| Example 38 | J-22 | A | A | A | A | A | A | A | A |
| Comparative Example 1 | CJ-1 | — | — | B | — | — | — | B | — |
| Comparative Example 2 | CJ-2 | — | — | B | — | — | — | B | — |
| Comparative Example 3 | CJ-3 | — | — | B | — | — | — | B | — |
| Comparative Example 4 | CJ-4 | — | — | B | — | — | — | B | — |
| Comparative Example 5 | CJ-5 | — | — | B | — | — | — | B | — |

As is clear from the results shown in Table 2, in the case of the ArF exposure, the radiation-sensitive resin compositions of Examples exhibited improved LWR performance, resolution and depth of focus, as compared with the radiation-sensitive resin compositions of Comparative Examples in any case of the development carried out with an alkali or an organic solvent, and some of the radiation-sensitive resin compositions of Examples gave "A" in the evaluation of the rectangularity of the cross-sectional shape. On the other hand, all of the radiation-sensitive resin compositions of Comparative Examples gave "B" in the evaluation of the rectangularity of the cross-sectional shape.

Preparation of Radiation-Sensitive Resin Composition (2)

Example 39

A radiation-sensitive resin composition (J-23) was prepared by mixing 100 parts by mass of (A-4) as the polymer (A), 3.6 parts by mass of (S-1) as the compound (B), 20 parts by mass of (C-1) as the acid generating agent (C), and 4,280 parts by mass of (F-1) and 1,830 parts by mass of (F-2) as the solvent (F).

Examples 40 to 60 and Comparative Examples 6 to 10

Radiation-sensitive resin compositions (J-24) to (J-44) and (CJ-6) to (CJ-10) were prepared in a similar manner to Example 39 except that the type and the content of each component used were as specified in Table 3 below.

TABLE 3

|  | Radiation-sensitive resin composition | (A) Polymer | | (B) Compound/ (D) Other acid diffusion control agent | | (C) Acid generating agent | | (F) Solvent | |
|---|---|---|---|---|---|---|---|---|---|
|  |  | type | content (parts by mass) | type | content (parts by mass) | type | content (parts by mass) | type | content (parts by mass) |
| Example 39 | J-23 | A-4 | 100 | S-1 | 3.6 | C-1 | 20 | F-1/F-2 | 4,280/1,830 |
| Example 40 | J-24 | A-4 | 100 | S-2 | 3.6 | C-1 | 20 | F-1/F-2 | 4,280/1,830 |
| Example 41 | J-25 | A-4 | 100 | S-3 | 3.6 | C-1 | 20 | F-1/F-2 | 4,280/1,830 |
| Example 42 | J-26 | A-4 | 100 | S-4 | 3.6 | C-1 | 20 | F-1/F-2 | 4,280/1,830 |
| Example 43 | J-27 | A-4 | 100 | S-5 | 3.6 | C-1 | 20 | F-1/F-2 | 4,280/1,830 |
| Example 44 | J-28 | A-4 | 100 | S-6 | 3.6 | C-1 | 20 | F-1/F-2 | 4,280/1,830 |
| Example 45 | J-29 | A-4 | 100 | S-7 | 3.6 | C-1 | 20 | F-1/F-2 | 4,280/1,830 |
| Example 46 | J-30 | A-4 | 100 | S-1 | 3.6 | C-2 | 20 | F-1/F-2 | 4,280/1,830 |
| Example 47 | J-31 | A-4 | 100 | S-1 | 3.6 | C-3 | 20 | F-1/F-2 | 4,280/1,830 |
| Example 48 | J-32 | A-4 | 100 | S-1 | 3.6 | C-2 | 20 | F-1/F-2 | 4,280/1,830 |
| Example 49 | J-33 | A-4 | 100 | S-1 | 3.6 | C-3 | 20 | F-1/F-2 | 4,280/1,830 |
| Example 50 | J-34 | A-4 | 100 | S-8 | 3.6 | C-1 | 20 | F-1/F-2 | 4,280/1,830 |
| Example 51 | J-35 | A-4 | 100 | S-9 | 3.6 | C-1 | 20 | F-1/F-2 | 4,280/1,830 |
| Example 52 | J-36 | A-4 | 100 | S-10 | 3.6 | C-1 | 20 | F-1/F-2 | 4,280/1,830 |
| Example 53 | J-37 | A-4 | 100 | S-11 | 3.6 | C-1 | 20 | F-1/F-2 | 4,280/1,830 |
| Example 54 | J-38 | A-4 | 100 | S-12 | 3.6 | C-1 | 20 | F-1/F-2 | 4,280/1,830 |
| Example 55 | J-39 | A-4 | 100 | S-13 | 3.6 | C-1 | 20 | F-1/F-2 | 4,280/1,830 |
| Example 56 | J-40 | A-4 | 100 | S-14 | 3.6 | C-1 | 20 | F-1/F-2 | 4,280/1,830 |
| Example 57 | J-41 | A-4 | 100 | S-15 | 3.6 | C-1 | 20 | F-1/F-2 | 4,280/1,830 |
| Example 58 | J-42 | A-4 | 100 | S-16 | 3.6 | C-1 | 20 | F-1/F-2 | 4,280/1,830 |
| Example 59 | J-43 | A-4 | 100 | S-1 | 1.8 | C-1 | 20 | F-1/F-2 | 4,280/1,830 |
|  |  |  |  | S-9 | 1.8 |  |  |  |  |
| Example 60 | J-44 | A-4 | 100 | S-1 | 1.8 | C-1 | 20 | F-1/F-2 | 4,280/1,830 |
|  |  |  |  | D-3 | 1.8 |  |  |  |  |
| Comparative Example 6 | CJ-6 | A-4 | 100 | D-1 | 3.6 | C-1 | 20 | F-1/F-2 | 4,280/1,830 |
| Comparative Example 7 | CJ-7 | A-4 | 100 | D-2 | 3.6 | C-2 | 20 | F-1/F-2 | 4,280/1,830 |

TABLE 3-continued

| Radiation-sensitive resin composition | (A) Polymer type | content (parts by mass) | (B) Compound/ (D) Other acid diffusion control agent type | content (parts by mass) | (C) Acid generating agent type | content (parts by mass) | (F) Solvent type | content (parts by mass) |
|---|---|---|---|---|---|---|---|---|
| Comparative Example 8 | CJ-8 | A-4 | 100 | D-3 | 3.6 | C-3 | 20 | F-1/F-2 | 4,280/1,830 |
| Comparative Example 9 | CJ-9 | A-4 | 100 | D-4 | 3.6 | C-2 | 20 | F-1/F-2 | 4,280/1,830 |
| Comparative Example 10 | CJ-1 | A-4 | 100 | D-5 | 3.6 | C-3 | 20 | F-1/F-2 | 4,280/1,830 |

Formation of Resist Pattern (3)

A resist film having a film thickness of 50 nm was provided on the surface of an 8-inch silicon wafer by applying each radiation-sensitive resin composition on the surface of the 8-inch silicon wafer using a spin coater (CLEAN TRACK ACTS, manufactured by Tokyo Electron Limited), then subjecting the same to PB at 90° C. for 60 sec, and cooling the same at 23° C. for 30 sec. Next, this resist film was irradiated with an electron beam using a simplified electron beam writer (model "HL800D", manufactured by Hitachi, Ltd.; output: 50 KeV, electric current density: 5.0 A/cm$^2$). After the irradiation, PEB was carried out at 120° C. for 60 sec. Thereafter, a development was carried out using a 2.38% by mass aqueous TMAH solution as an alkaline developer solution at 23° C. for 30 sec, followed by washing with water and drying to form a positive type resist pattern.

Evaluations

Measurements were made on the resist patterns obtained in Formation of Resist Pattern (3) described above in accordance with methods similar to those described above to evaluate the LWR performance, the resolution and the cross-sectional shape of each radiation-sensitive resin composition. The results of the evaluations are shown in Table 4. It is to be noted that comparisons were made with, as a standard: Comparative Example 6 for Examples 39 to 45 and 50 to 60; Comparative Example 7 for Example 46; Comparative Example 8 for Example 47; Comparative Example 9 for Example 48; and Comparative Example 10 for Example 49, whereby evaluations were made. In Table 4, "—" denotes being a decision standard.

TABLE 4

| | Radiation-sensitive resin composition | LWR performance | Resolution | Rectangularity of cross-sectional shape |
|---|---|---|---|---|
| Example 39 | J-23 | A | A | A |
| Example 40 | J-24 | A | A | B |
| Example 41 | J-25 | B | A | A |
| Example 42 | J-26 | B | A | A |
| Example 43 | J-27 | A | B | B |
| Example 44 | J-28 | A | A | A |
| Example 45 | J-29 | A | B | A |
| Example 46 | J-30 | A | A | B |
| Example 47 | J-31 | A | A | A |
| Example 48 | J-32 | A | B | A |
| Example 49 | J-33 | A | A | A |
| Example 50 | J-34 | A | A | A |
| Example 51 | J-35 | A | A | A |
| Example 52 | J-36 | A | A | A |
| Example 53 | J-37 | A | A | A |
| Example 54 | J-38 | B | B | B |
| Example 55 | J-39 | B | B | B |
| Example 56 | J-40 | B | B | B |
| Example 57 | J-41 | A | A | A |
| Example 58 | J-42 | B | B | B |
| Example 59 | J-43 | A | A | A |
| Example 60 | J-44 | A | A | A |
| Comparative Example 6 | CJ-6 | — | — | B |
| Comparative Example 7 | CJ-7 | — | — | B |
| Comparative Example 8 | CJ-8 | — | — | B |
| Comparative Example 9 | CJ-9 | — | — | B |
| Comparative Example 10 | CJ-10 | — | — | B |

As is clear from the results shown in Table 4, in the case where the exposure was carried out using an electron beam and a development was carried out with an alkali, the radiation-sensitive resin compositions of Examples exhibited improved LWR performance and resolution, as compared with Comparative Examples, and some of the radiation-sensitive resin compositions of Examples gave "A" in the evaluation of the rectangularity of the cross-sectional shape. On the other hand, all of the radiation-sensitive resin compositions of Comparative Examples gave "B" in the evaluation of the rectangularity of the cross-sectional shape.

The radiation-sensitive resin composition and the resist pattern-forming method according to the embodiments of the present invention enable a resist pattern having a small LWR, high resolution, and superior rectangularity of a cross-sectional shape to be formed while exhibiting a great depth of focus. The acid diffusion control agent according to the embodiment of the present invention can be suitably used as a component of the radiation-sensitive resin composition. The compound according to the embodiment of the present invention can be suitably used as the acid diffusion control agent according to the embodiment of the present invention. The method for producing a compound according to the embodiment of the present invention enables the compound to be produced conveniently in a favorable yield. Therefore, these can be suitably used in processes for production of semiconductor devices, and the like, in which further progress of miniaturization is expected in the future.

Obviously, numerous modifications and variations of the present invention are possible in light of the above teachings. It is therefore to be understood that within the scope of the appended claims, the invention may be practiced otherwise than as specifically described herein.

The invention claimed is:

1. A radiation-sensitive resin composition comprising:
a polymer that comprises a structural unit that comprises an acid-labile group; and
a compound represented by formula (1):

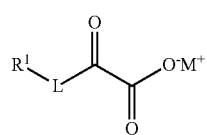

(1)

wherein in the formula (1),
$R^1$ represents a monovalent organic group having 1 to 30 carbon atoms;
L represents a single bond, an oxygen atom or a sulfur atom; and
$M^+$ represents a monovalent radioactive ray-labile onium cation which is labile to a KrF excimer laser, an ArF excimer laser, an electron beam or an EUV, and
in a case where L represents a single bond, the monovalent radioactive ray-labile onium cation represented by $M^+$ is represented by formula (X):

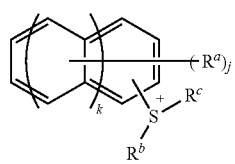

(X)

wherein in the formula (X),
$R^a$ represents a fluorine atom, a hydroxy group, an alkyl group having 1 to 10 carbon atoms, an alkoxy group having 1 to 10 carbon atoms, an alkoxycarbonyl group having 2 to 11 carbon atoms or an alkylsulfonyl group having 1 to 10 carbon atoms;
j is an integer of 0 to 9, wherein in a case where j is no less than 2, a plurality of $R^a$s are each identical or different;
$R^b$ and $R^c$ each independently represent a substituted or unsubstituted alkyl group having 1 to 10 carbon atoms or a substituted or unsubstituted aryl group having 6 to 20 carbon atoms, or $R^b$ and $R^c$ taken together represent a ring structure having 4 to 10 ring atoms together with the sulfur atom to which $R^b$ and $R^c$ bond; and
k is an integer of 0 to 2.

2. The radiation-sensitive resin composition according to claim 1, wherein the monovalent organic group represented by $R^1$ in the formula (1) is a monovalent hydrocarbon group or a monovalent fluorinated hydrocarbon group, and L represents the single bond.

3. The radiation-sensitive resin composition according to claim 1, wherein the monovalent organic group represented by $R^1$ in the formula (1) is a monovalent hydrocarbon group, a monovalent fluorinated hydrocarbon group, a monovalent aliphatic heterocyclic group or a monovalent fluorinated aliphatic heterocyclic group, and L represents the oxygen atom or the sulfur atom.

4. The radiation-sensitive resin composition according to claim 1, wherein the monovalent radioactive ray-labile onium cation represented by $M^+$ is represented by formula (X).

5. The radiation-sensitive resin composition according to claim 1, further comprising a radiation-sensitive acid generator.

6. The radiation-sensitive resin composition according to claim 1, wherein the structural unit is represented by formula (2-1):

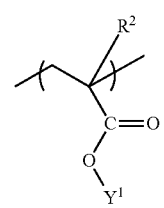

(2-1)

wherein in the formula (2-1),
$R^2$ represents a hydrogen atom, a fluorine atom, a methyl group or a trifluoromethyl group; and
$Y^1$ is a monovalent acid-labile group represented by formula (Y-1):

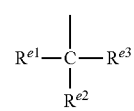

(Y-1)

wherein in the formula (Y-1),
$R^{e1}$ represents a monovalent hydrocarbon group having 1 to 20 carbon atoms;
$R^{e2}$ and $R^{e3}$ each independently represent a monovalent chain hydrocarbon group having 1 to 10 carbon atoms or a monovalent alicyclic hydrocarbon group having 3 to 20 carbon atoms, or $R^{e2}$ and $R^{e3}$ taken together represent an alicyclic structure having 3 to 20 ring carbon atoms together with the carbon atom to which $R^{e2}$ and $R^{e3}$ bond.

7. The radiation-sensitive resin composition according to claim 1, wherein the polymer further comprises a structural unit represented by formula (4):

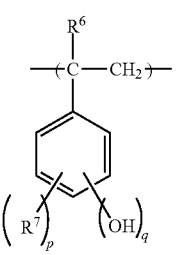

(4)

wherein in the formula (4),
$R^6$ represents a hydrogen atom or a methyl group;
$R^7$ represents a monovalent organic group having 1 to 20 carbon atoms;
p is an integer of 0 to 3, wherein in a case where $R^7$ is present in a plurality of number, a plurality of $R^7$s are each identical or different; and q is an integer of 1 to 3, wherein a sum of p and q is no greater than 5.

8. A resist pattern-forming method comprising:
applying the radiation-sensitive resin composition according to claim 1 directly or indirectly on a substrate to form a resist film;
exposing the resist film; and
developing the exposed resist film.

9. The radiation-sensitive resin composition according to claim 1, wherein an amount of the compound is from 0.1 parts to 30 parts by mass with respect to 100 parts by mass of the polymer.

10. The radiation-sensitive resin composition according to claim 1, wherein an amount of the compound is from 1 part to 5 parts by mass with respect to 100 parts by mass of the polymer.

11. An acid diffusion control agent comprising a compound represented by formula (1):

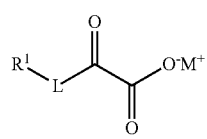

(1)

wherein in the formula (1),
$R^1$ represents a monovalent organic group having 1 to 30 carbon atoms;
L represents a single bond, an oxygen atom or a sulfur atom; and
$M^+$ represents a monovalent radioactive ray-labile onium cation which is labile to a KrF excimer laser, an ArF excimer laser, an electron beam or an EUV, and
in a case where L represents a single bond, the monovalent radioactive ray-labile onium cation represented by $M^+$ is represented by formula (X):

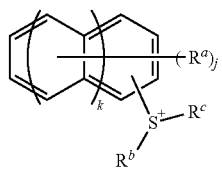

(X)

wherein in the formula (X),
$R^a$ represents a fluorine atom, a hydroxy group, an alkyl group having 1 to 10 carbon atoms, an alkoxy group having 1 to 10 carbon atoms, an alkoxycarbonyl group having 2 to 11 carbon atoms or an alkylsulfonyl group having 1 to 10 carbon atoms;
j is an integer of 0 to 9, wherein in a case where j is no less than 2, a plurality of $R^a$s are each identical or different;
$R^b$ and $R^c$ each independently represent a substituted or unsubstituted alkyl group having 1 to 10 carbon atoms or a substituted or unsubstituted aryl group having 6 to 20 carbon atoms, or $R^b$ and $R^c$ taken together represent a ring structure having 4 to 10 ring atoms together with the sulfur atom to which $R^b$ and $R^c$ bond; and
k is an integer of 1 or 2.

12. A compound represented by formula (1):

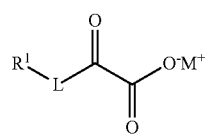

(1)

wherein in the formula (1),
$R^1$ represents a monovalent organic group having 1 to 30 carbon atoms;
L represents a single bond, an oxygen atom or a sulfur atom; and
$M^+$ represents a monovalent radioactive ray-labile onium cation which is labile to a KrF excimer laser, an ArF excimer laser, an electron beam or an EUV, and
in a case where L represents a single bond, the monovalent radioactive ray-labile onium cation represented by $M^+$ is represented by formula (X):

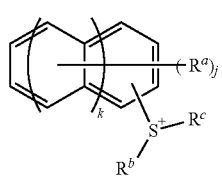

(X)

wherein in the formula (X),
$R^a$ represents a fluorine atom, a hydroxy group, an alkyl group having 1 to 10 carbon atoms, an alkoxy group having 1 to 10 carbon atoms, an alkoxycarbonyl group having 2 to 11 carbon atoms or an alkylsulfonyl group having 1 to 10 carbon atoms;
j is an integer of 0 to 9, wherein in a case where j is no less than 2, a plurality of $R^a$s are each identical or different;
$R^b$ and $R^c$ each independently represent a substituted or unsubstituted alkyl group having 1 to 10 carbon atoms or a substituted or unsubstituted aryl group having 6 to 20 carbon atoms, or $R^b$ and $R^c$ taken together represent a ring structure having 4 to 10 ring atoms together with the sulfur atom to which $R^b$ and $R^c$ bond; and
k is an integer of 1 or to 2.

13. The compound according to claim 12, wherein the monovalent organic group represented by $R^1$ in the formula (1) is a monovalent hydrocarbon group or a monovalent fluorinated hydrocarbon group, and L represents the single bond.

14. The compound according to claim 12, wherein the monovalent organic group represented by $R^1$ in the formula (1) is a monovalent hydrocarbon group, a monovalent fluorinated hydrocarbon group, a monovalent aliphatic heterocyclic group or a monovalent fluorinated aliphatic heterocyclic group, and L represents the oxygen atom or the sulfur atom.

15. The compound according to claim 12, wherein the monovalent radioactive ray-labile onium cation represented by $M^+$ is represented by formula (X).

* * * * *